(12) United States Patent
Gold et al.

(10) Patent No.: US 9,624,235 B2
(45) Date of Patent: Apr. 18, 2017

(54) COMPOUNDS AND METHODS FOR INHIBITION OF AP ENDONUCLEASE-1/REDOX FACTOR-1 (HAPE1) ACTIVITY

(71) Applicant: University of Pittsburgh—Of the Commonwealth System of Higher Education, Pittsburgh, PA (US)

(72) Inventors: Barry I. Gold, Pittsburgh, PA (US); Xiangqun Xie, Pittsburgh, PA (US); Ajay Srinivasan, Mumbai (IN); LiRong Wang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/374,516

(22) PCT Filed: Jan. 29, 2013

(86) PCT No.: PCT/US2013/023653
§ 371 (c)(1),
(2) Date: Jul. 24, 2014

(87) PCT Pub. No.: WO2013/116228
PCT Pub. Date: Aug. 8, 2013

(65) Prior Publication Data
US 2014/0371259 A1    Dec. 18, 2014

Related U.S. Application Data

(60) Provisional application No. 61/593,276, filed on Jan. 31, 2012.

(51) Int. Cl.
| | | |
|---|---|---|
| *C07D 491/056* | (2006.01) | |
| *A61K 31/4355* | (2006.01) | |
| *A61K 31/4741* | (2006.01) | |
| *A61K 31/4709* | (2006.01) | |
| *A61K 45/06* | (2006.01) | |

(52) U.S. Cl.
CPC ...... *C07D 491/056* (2013.01); *A61K 31/4355* (2013.01); *A61K 31/4709* (2013.01); *A61K 31/4741* (2013.01); *A61K 45/06* (2013.01); *C12Y 402/99018* (2013.01)

(58) Field of Classification Search
CPC ............ C07D 491/056; A61K 31/4741; A61K 31/4355; A61K 31/4709
USPC ............................................ 546/90; 514/291
See application file for complete search history.

(56) References Cited

U.S. PATENT DOCUMENTS 8,440,692 B2 *  5/2013  Kuo et al. ............... 514/312

OTHER PUBLICATIONS

Caplus Englis abstract AN 1984:563275 Pellerano C et al DN 101:163275 , 1984.*
Ajay Srinivasan et al, Apr. 2012, Identifiation and Characterization of Human Apurinic/Apyrimidinic Endonuclease-1 Inhibitors.*
Pellerano C et al , II Farmaco-Ed, Sc vol. 39—fasc. 7 , 1984.*
Bapat et al. "Novel small molecule inhibitor of Ape1 endonuclease blocks proliferation and reduces viability of glioblastoma cells", *J. Pharmacol. Exp. Ther.*, 334(3): 988-998, 2010.
International Search Report and Written Opinion from International application No. PCT/US2013/023653, dated May 30, 2013, 4pp.
Madhusudan et al. "Isolation of a small molecule inhibitor of DNA base excision repair", *Nucleic Acids Res.*, 33(15): 4711-4724, 2005.
Simeonov et al. Identification and characterization of inhibitors of human apurinic/apyrimidinic endonuclease APE1. *PLoS One*, 4(6): 13pp, 2009.
Srinivasan et al. "Identification and characterization of human apurinic/apyrimidinic endonuclease-1 inhibitors," *Biochemistry*, 51(31): 6246-59, Aug. 7, 2012.

* cited by examiner

*Primary Examiner* — Rita Desai
(74) *Attorney, Agent, or Firm* — Klarquist Sparkman, LLP

(57) ABSTRACT

A method for treating a neoplasm in a subject, comprising co-administering to the subject a therapeutically effective amount of an anticancer agent and a substituted 6,7-methylenedioxy-4-amino-quinoline, or a pharmaceutically acceptable salt or ester thereof.

5 Claims, 14 Drawing Sheets

FIG. 10A
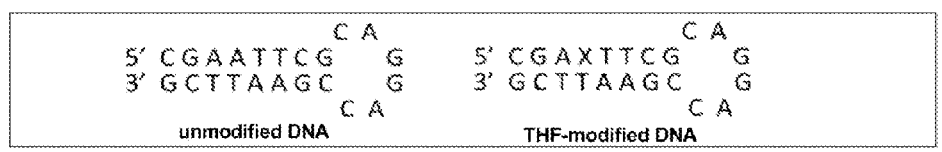
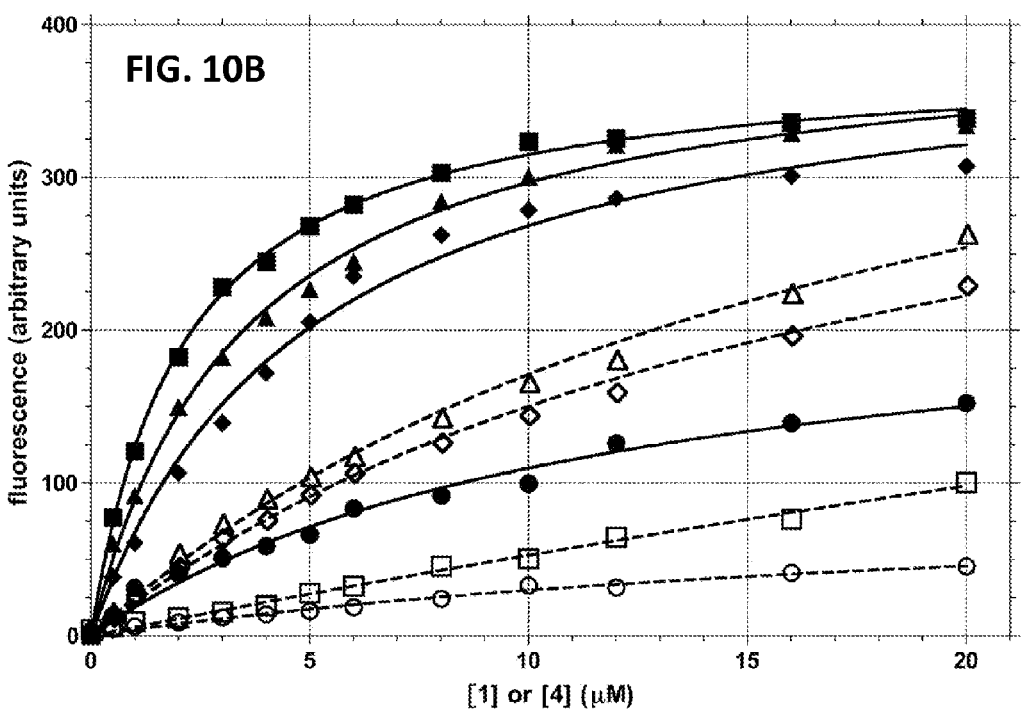
FIG. 10B

COMPOUNDS AND METHODS FOR INHIBITION OF AP ENDONUCLEASE-1/REDOX FACTOR-1 (HAPE1) ACTIVITY

CROSS REFERENCE TO RELATED APPLICATIONS

This application is the U.S. National Stage of International Application No. PCT/US2013/023653, filed Jan. 29, 2013, which was published in English under PCT Article 21(2), which in turn claims the benefit of U.S. Provisional Application No. 61/593,276, filed Jan. 31, 2012, which is incorporated herein by reference in its entirety.

BACKGROUND

The human apurinic/apyrimidinic endonclease-1/redox factor-1 (APE1) protein is associated with the processing of abasic DNA sites via the base excision repair pathway and with the transcriptional activation of genes associated with redox regulation. The genetic deletion of APE1 is lethal both in vitro and in vivo, presumably as a result of the formation of the 10,000 abasic sites the form per cell per day. Accordingly, efforts have been made to develop small molecules that can inhibit APE1 activity in a controlled fashion. Such molecules will be useful tools to understand the multiple functions of the protein and how it interacts with other proteins and pathways. From a therapeutic standpoint, these small molecule inhibitors may be exploited to overcome the resistance of some tumor cells to DNA damaging agents that results from overexpression of base excision repair pathway proteins.

Prior attempts to generate small molecule inhibitors of APE1 have had some limited success. In one case, the results with indolecarboxamide based molecules have been difficult to reproduce. The inhibitory molecules are generally dicarboxylic acids or related analogs that mimic the (—O—PO$_2$—O—R—O—PO$_2$O—)—2 diphosphate substrate of the enzyme. In another study, the molecules, also dianionic, inhibitors based on arylstibinic acids, lacked activity in cells despite their excellent activity against the protein in a biochemical assay. In a third study, compounds from the Sigma-Aldrich Library of Pharmacologically Active Compounds (LOPAC) were screened and some active compounds identified. One compound that has been pursued is 7-nitro-1H-indole-2-carboxylic acid.

Although technically not an inhibitors of APE1 activity, methoxylamine (MeONH$_2$) binds to the aldehyde in the ring-opened form of the AP site to yield a stable methoxyoxime derivative that cannot be processed by APE1. Accordingly, there have been attempts to clinically use MeONH$_2$ in Phase I trials to enhance the cytoxicity of DNA damaging drugs that induce AP sites as repair intermediates.

In general, all prior attempts to generate inhibitors of APE1 have led to molecules with no activity in cells or low specificity.

SUMMARY

Disclosed herein in one embodiment is a method of inhibiting AP endonuclease-1/redox factor-1 (hAPE1) activity comprising application of a compound having the structure

wherein domain A has the structure

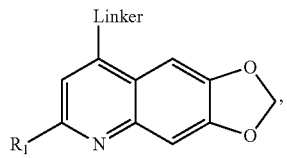

wherein $R_1$ is H, a C1-C5 alkyl group, which can be branched, unbranched, cyclic or acyclic, or a 3-5 member ring, which can be homocyclic or heterocyclic; the linker is a flexible or rigid linking group; and domain B includes a portion that is suitable to form a π-cation interaction with Arg177.

Also disclosed herein is a method for treating cancer in a subject, comprising co-administering to the subject a DNA damaging anticancer agent and a compound having a structure of:

wherein domain A has the structure

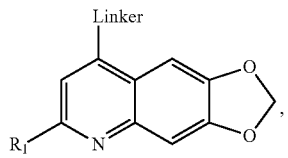

wherein $R_1$ is H, a C1-C5 alkyl group, which can be branched, unbranched, cyclic or acyclic, or a 3-5 member ring, which can be homocyclic or heterocyclic; the linker is a flexible or rigid linking group; and domain B includes a portion that is suitable to form a π-cation interaction with Arg177.

Further disclosed herein is a method for enhancing the toxicity of a DNA methylating agent in a cell, comprising contacting the cell with a DNA alkylating agent and a compound having a structure of:

wherein domain A has the structure

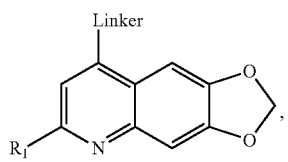

wherein R$_1$ is H, a C1-C5 alkyl group, which can be branched, unbranched, cyclic or acyclic, or a 3-5 member ring, which can be homocyclic or heterocyclic; the linker is a flexible or rigid linking group; and domain B includes a portion that is suitable to form a π-cation interaction with Arg177.

According to another disclosed embodiment, there is provided a method for treating a neoplasm in a subject, comprising co-administering to the subject a therapeutically effective amount of an anticancer agent and a substituted 6,7-methylenedioxy-4-amino-quinoline, or a pharmaceutically acceptable salt or ester thereof.

Further disclosed herein is a method for treating a neoplasm in a subject, comprising administering to the subject a therapeutically effective amount of a substituted 6,7-methylenedioxy-4-amino-quinoline, or a pharmaceutically acceptable salt or ester thereof.

Additionally disclosed herein is a method of inhibiting AP endonuclease-1/redox factor-1 (hAPE1) activity, comprising contacting hAPE1 with a substituted 6,7-methylenedioxy-4-amino-quinoline, or a pharmaceutically acceptable salt or ester thereof.

Also disclosed herein is a compound, or a pharmaceutically acceptable salt or ester thereof, having a structure of:

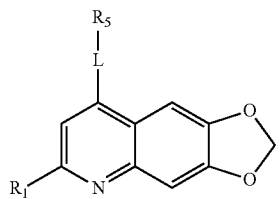

wherein R$_1$ is H, optionally substituted alkyl, optionally substituted cycloalkyl, optionally substituted aryl, cyano, optionally substituted heterocyclic, halogen, optionally substituted alkoxy, optionally substituted amino, or optionally substituted cycloalkoxy;
L is linking group; and
R$_5$ is selected from:

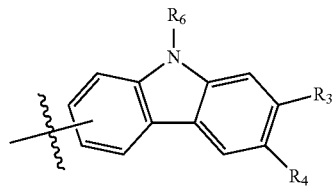

wherein R$_3$ and R$_4$ are each independently selected from H, optionally substituted alkyl, optionally substituted cycloalkyl, optionally substituted aryl, optionally substituted heterocyclic, optionally substituted alkoxy, halogen, optionally substituted aryloxy, or optionally substituted cycloalkoxy; and
R$_6$ is H, optionally substituted alkyl, optionally substituted cycloalkyl, optionally substituted aryl, optionally substituted alkoxy, optionally substituted cycloalkoxy, optionally substituted amino, or optionally substituted aryloxy; provided that at least one of the following substitutions is present:
(i) R$_1$ is optionally substituted alkyl or halogen;
(ii) R$_6$ is methyl; and/or
(iii) R$_3$ and R$_4$ are each independently selected from optionally substituted alkyl, optionally substituted cycloalkyl, optionally substituted aryl, optionally substituted heterocyclic, optionally substituted alkoxy, halogen, or optionally substituted aryloxy.

The foregoing and will become more apparent from the following detailed description, which proceeds with reference to the accompanying figures.

BRIEF DESCRIPTION OF THE DRAWINGS

FIG. 1(a) The entire protein with inhibitor 4 bound with carbazole ring showing. FIG. 1(b) Closeup of the complex showing Arg177 making a cation-pi interaction with the carbazole heterocycle and the potential for additional groups on the 2-methyl position of the quinoline ring. FIG. 1(c) Closeup of inhibitor 4 and residues that line the binding pocket with H-bond interactions with N$^{174}$ (2.5 Å), T$^{268}$ (3.1 Å), hydrophobic interactions between F$^{266}$ and L$^{282}$ and cation-π interaction between the carbazole ring and Arg177 that is stacked upon it. FIG. 1(d) Relaxed sterioview of how inhibitor 4 fills the binding pocket and the possibility of adding hydrophobic groups onto the 6- and/or 7-positions of the carbazole ring. The H-bond between the hydrazone N—H and Thr is shown (yellow arrow).

FIG. 10. The interaction of compounds 1 and 4 with DNA was evaluated by changes in their fluorescence in the absence and presence of EtBr: (A) sequence of DNA hairpins used in the fluorescence measurements (X=THF abasic site); (B) Fluorescence of compounds 1 (395 nm excitation and 460 nm emission) and 4 (400 nm excitation and 500 nm emission) with 0.5 µM DNA was evaluated by fluorescence increases in the absence (●, 1 with unmodified DNA; ■, 1 with THF modified DNA; ◆, 4 with unmodified DNA; ▲, 4 with THF modified DNA) and presence of 4 µM EtBr (○, 1 with unmodified DNA and EtBr; □, 1 with THF modified DNA and EtBr; ◇, 4 with unmodified DNA and EtBr; Δ, 4 with THF modified DNA and EtBr).

DETAILED DESCRIPTION

Terminology

Figure 1C:
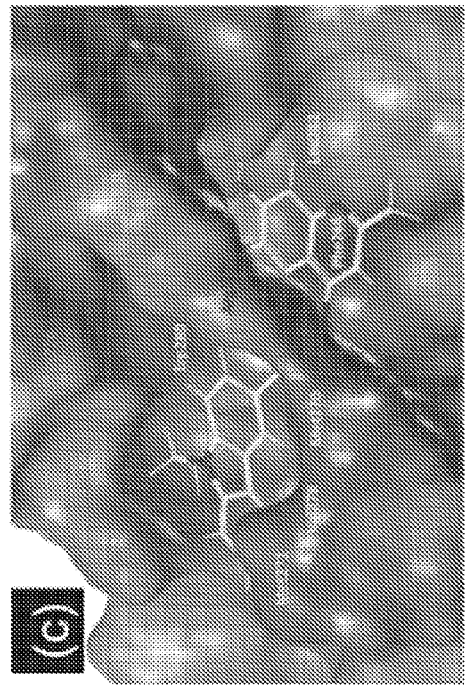
FIGS. 1(a)-(d) depicts modeling of APE1 binding of an APE1 inhibitor disclosed herein (compound 4, Table 1). Inhibitor 4 is complexed with APE1. The DNA and AP site were removed from the structure and the inhibitor docked into the cavity.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms. The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aminoalkyl" refers to alkyl groups as defined above where at least one hydrogen atom is replaced with an amino group (e.g, —$CH_2$—$NH_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

The term "carboxylate" or "carboxyl" refers to the group —$COO^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. The hAPE1 inhibitor disclosed herein and the anticancer agent may be included in the same composition or they may each individually be included in separate compositions. In certain embodiments, the two agents may be administered during a time frame wherein their respective periods of biological activity overlap. Thus, the term includes sequential as well as coextensive administration of two or more agents.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

The term "neoplasm" refers to an abnormal cellular proliferation, which includes benign and malignant tumors, as well as other proliferative disorders.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_1$-$C_6$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. For example, a therapeutically effective amount may be an amount of a hAPE1 inhibitor that is sufficient to enhance the efficacy of a co-administered anticancer agent. A therapeutically effective amount may also be an amount of a hAPE1 inhibitor that is sufficient to inhibit a neoplasm in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits food intake or weight gain in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

The sequence (SEQ ID1) of APE protein is provided below:

MPKRGKKGAVAEDGDELRTEPEAKKSKTAAKKNDKEAAGEGPALYE

DPPDQKTSPSGKPATLKICSWNVDGLRAWIKKKGLDWVKEEAPDIL

CLQETKCSENKLPAELQELPG LSHQYWSAPSDKEGYSGVGLLSRQ

CPLKVSYGIGDEEHDQEGRVIVAEFDSFVLVTAYVPNAGRGLVRLE

YRQRWDEAFRKFLKGLASRKPLVLCGDLNVAHEEIDLRNPKGN KK

NAGFTPQERQGFGELLQAVPLADSFRHLYPNTPYAYTFWTYMMNAR

SKNVGWRLDYFLLSHSLLPALCDSKIRSKALGSDHCPITLYLAL

Compounds

The endonuclease function of APE-1 is located toward the C-terminus of the protein. The N-terminal domain is associated with the redox center (a.k.a., Ref-1) that regulates the activity of specific transcriptional factors by maintaining them in a reduced state. In addition, APE-1 has been linked to several other functions, including RNA processing and in $Ca^{2+}$-dependent gene expression and regulation. The lethality of APE-1 knockouts has been attributed to loss of the repair activity, and the mechanism of cell death involves apoptosis. Over-expression of APE-1 makes cells resistant to alkylating agents. There is also evidence that APE-1 expression can be induced by genotoxic agents, including cancer drugs. These data raise the question of whether APE-1 expression is associated with tumor resistance to DNA damaging agents. In this regard, the lethality of clinically used anticancer treatments can be enhanced by a temporal decrease in APE-1 using antisense technology. Therefore, molecules that modulate APE-1 activity could be important adjuvants to clinically used DNA damaging antineoplastic agents. Recently, it has been reported that inhibitors of APE-1 endonuclease activity can create a synthetic lethality in cells defective in double-strand break repair, i.e., BRCA1, BRCA2 and ATM. This result is not unexpected since homologous recombination (HR) mutants are particularly sensitive to methylation damage repaired by BER. In fact, yeast cells that lack HR tolerate DNA alkylation damage better if there is no BER, indicating the biological consequences of BER in the absence of HR. This result with APE-1 induced synthetic lethality is similar to the interaction between BRCA defective cells and PARP inhibitors.

Human apurinic/apyrmidinic endonuclease-1/redox factor-1 (hAPE1) is a critical protein associated with the processing of abasic site lesions that develop spontaneously and/or as a result of base excision repair (BER) at the rate of approximately 104 lesions/day/cell. The protein is overexpressed in a number of tumor cells and is associated with the resistance of some tumors to chemotherapeutic agents that act via damaging DNA. Therefore, inhibition of APE1 activity using small molecules presents an attractive approach to enhance the therapeutic effectiveness of clinically used DNA damaging drugs. Disclosed herein are novel nM APE1 inhibitors identified through a combination of reiterative molecular modeling and chemical screening using molecular beacon and excision assays. The molecules bind with nM affinity to the purified hAPE1 protein and do not affect the redox activity of the APE1 protein. They have an $LD_{50}$ of approximately 1 µM in human T98G glioma cells in the absence of DNA alkylating agents. However, subtoxic concentrations of inhibitor have a potent enhancing effect on the toxicity of Me-lex, which is a DNA methylating agent that selectively and efficiently generates N3-methyladenine (3-mA). 3-mA is converted into an abasic site by alkyladenine-DNA glycosylase, so the enhancing effect of the inhibitor on Me-lex toxicity is consistent with a decrease in APE1 activity via diminished BER.

The compounds disclosed herein are distinct from previously reported APE1 inhibitors. For example, a new class of compounds disclosed herein inhibit APE1 activity in vitro and in cells, and potentiate the toxicity of, for example, a methylating agent that selectively generates 3-methyladenine (3-mA), which is a substrate for human alkyladenine-DNA glycosylase (hAAG) and base excision repair.

The empirical structure of the inhibitors of APE-1 protein may, for example, be dissected into two major regions called "Domain A" and "Domain B" which are linked together by a linker

In a number of studied embodiments, domain A was more conserved across many representatives of the molecular family studied, whereas Domain B appears to be more diverse and tolerant to changes in molecular structure as well as functional groups. In general, the linker may, for example, be flexible or rigid. Rigid linkers may, for example, assist in maintaining the molecule in a desired conformation. In a number of embodiments, linkers including carbon-carbon and/or carbon-nitrogen bonds are present. In a number of embodiments the linker has the formula $C_xN_y$, wherein x and y are integers and x+y is in the range of 2 to 5, 3 to 5 or 3 to 4. Linkers of similar length to such a linker may also be suitable. In general, single bonds in the linker provide for substantial rotation, while double bonds and cyclic or ring structures in the linker restrict rotation/conformation. In a number of embodiments, a 5 or 6-member ring is present in the linker to make the linker more rigid. One may, for example, be able to trap a compound hereof in a desired conformation (for example, a most significant or active conformation). One bond or two or three bonds adjacent bonds may, for example, be trapped within a ring system.

In a number of embodiments the linker includes the group —N(H)— attached is to Domain A, (for example, to a quinoline ring structure of Domain A). In a number of embodiments, a hydrazone linker is used. In a number of embodiments, the hydrazone linker region was well conserved.

A molecular dissection of an embodiment of a typical inhibitor follows. It is understood that the discussed molecular structures are representative only and may not reflect all the observed functional groups that are actually tethered in the actual molecules.

An embodiment of Domain A is illustrated below with a hydrazone linker

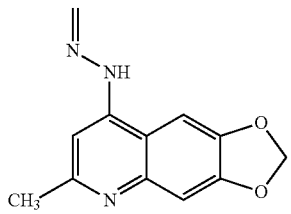 [SMILES: C=NNc1cc(C)nc2cc3c(cc12)OCO3]

An embodiment of Domain B is illustrated below with a hydrazone linker

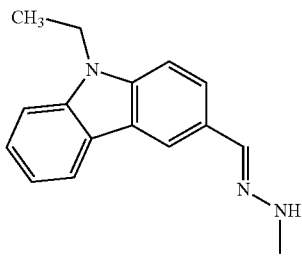 [SMILES: CCn1c2ccccc2c2cc(/C=N/NC)ccc21]

A partially generalized formula for an inhibitor molecule hereof including Domain A and Domain B as described above is provided below

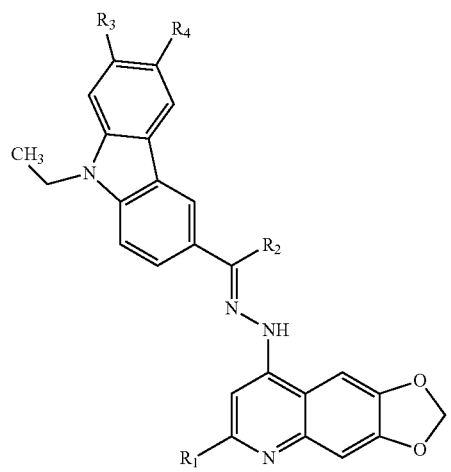

In a number of embodiments of the above molecule, Domain A was more conserved across all APE inhibitors studied. Absence of this domain was observed experimentally to substantially diminish the APE-1 inhibitory activity in a number of studies.

Asn229 of the APE protein is within 3A° of one of the oxygens in the methylenedioxy ring and Thr268 amide carbonyl may, for example, make an H-bond with the H—N on the hydrazone linker A proposed model indicates that the 2-methyl group on the quinoline ring in the specific embodiment illustrated may be enlarged. That is, in a number of embodiments, $R_1$ in the generalized structure may, for example, be a number of alkyl groups and other groups. In a number of embodiments $R_1$ is a H or a $C_1$-$C_5$ alkyl group, which may, for example, be branched, unbranched, cyclic or acyclic. $R_1$ may, for example, be a 3-5 member ring, which may, for example, be homocyclic or heterocyclic. In a number of embodiments of heterocyclic rings, the heteroatom(s) is/are nitrogen, oxygen, or sulfur. In a number of embodiments, the heteroatom(s) is/are nitrogen or oxygen. In a number of embodiments $R_1$ was —$CH_3$.

In a number of embodiments, $R_2$ may, for example, be H, or a C1-C5 branched, unbranched, cyclic or acyclic alkyl group. In a number of embodiments, $R_2$ was H or —$CH_3$.

Diverse functional groups and modifications are tolerated in Domain B as observed experimentally.

The flexible Arg177 in the active site of APE protein, is predicted to move into a position similar to that in the APE1-DNA complex and stack on the carbazole ring variant of Domain B—this would lead to strong π-cation interactions. In general, and without limitation to any specific mechanism, Domain B includes a portion or group that is suitable to form a π-cation interaction with Arg177 (+/−2). The positive cation is a side chain Arg177 having an $NH_3^+$ group.

In certain embodiments, the inhibitors are substituted 6,7-methylenedioxy-4-amino-quinolines, or a pharmaceutically acceptable salts or esters thereof, having a structure of:

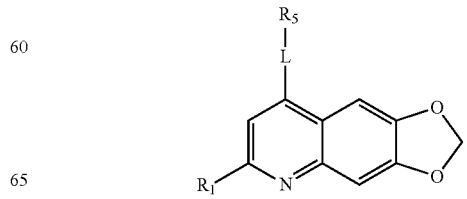

wherein $R_1$ is H, optionally substituted alkyl, optionally substituted cycloalkyl, optionally substituted aryl, cyano, optionally substituted heterocyclic, halogen, optionally substituted alkoxy, optionally substituted cycloalkoxy, optionally substituted amino, or optionally substituted aryloxy;
L is linking group; and
$R_5$ is selected from:

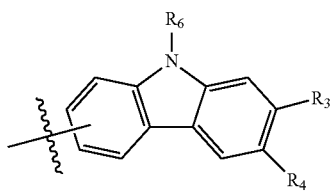

wherein $R_3$ and $R_4$ are each independently selected from H, optionally substituted alkyl, optionally substituted cycloalkyl, optionally substituted aryl, optionally substituted heterocyclic, optionally substituted alkoxy, halogen, or optionally substituted aryloxy; and $R_6$ is H, optionally substituted alkyl, optionally substituted cycloalkyl, optionally substituted aryl, optionally substituted alkoxy, optionally substituted cycloalkoxy, optionally substituted amino, or optionally substituted aryloxy;

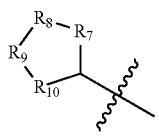

wherein $R_7$, $R_8$, $R_9$, and $R_{10}$ are each independently selected from optionally substituted C, optionally substituted N, optionally substituted O, or optionally substituted S, provided at least two of $R_7$, $R_8$, $R_9$, and $R_{10}$ are optionally substituted C; and the $R_7$-$R_{10}$ ring is non-aromatic, partially aromatic, or fully aromatic; or

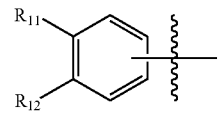

wherein $R_{11}$ and $R_{12}$ are each independently H, optionally substituted alkyl, optionally substituted cycloalkyl, optionally substituted aryl, optionally substituted alkoxy, optionally substituted cycloalkoxy, or $R_{11}$ and $R_{12}$ together form a 5-membered or 6-membered optionally substituted aryl, optionally substituted heteroaryl, optionally substituted cycloalkyl, or optionally substituted heterocycloalkyl.

In the specific embodiments set forth herein, and without limitation to any specific mechanism, the model indicates that hydrophobic substitutions on the 6- and/or 7-positions (that is, $R_3$ and $R_4$) of the carbazole may fill the remaining vacancy in the binding pocket of the APE-1 protein. In a number of embodiments $R_3$ and $R_4$ are, independently, a C1-C5 alkyl group, which may, for example, be branched, unbranched, cyclic or acyclic. $R_1$ may also, for example, be a 3-5 member ring, which may, for example, homocyclic or heterocyclic. In a number of embodiments of heterocyclic rings, the heteroatom(s) is/are nitrogen, oxygen, or sulfur. In a number of embodiments, the heteroatom(s) is/are nitrogen or oxygen.

Some representative substitutions are illustrated below:

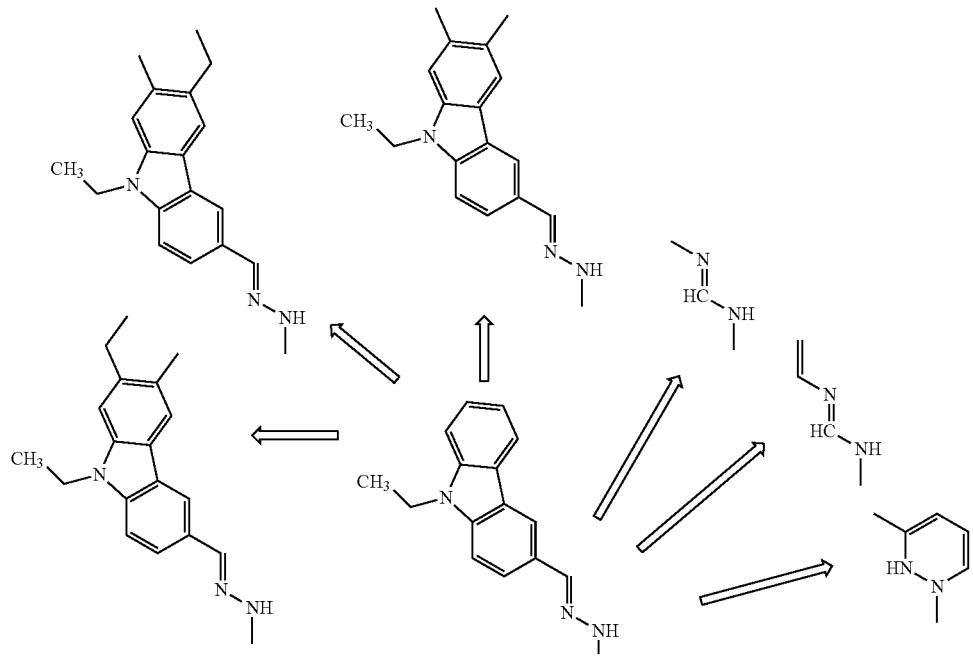

-continued

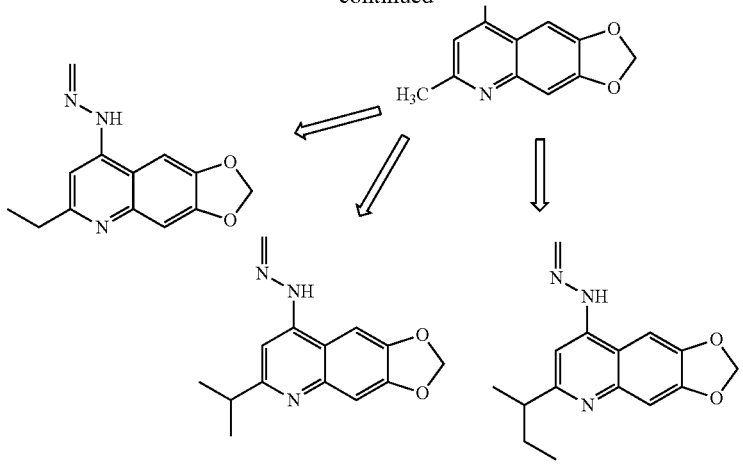

In certain embodiments, the 2-position on the quinoline ring and the 7- and/or 8-position on the carbazole heterocycle of the inhibitor 4 may, for example, be modified via hydrophobic or hydrophilic groups, which may improve the binding affinity. In certain embodiments, the molecules may be further altered by converting the potentially problematic hydrazone functionality that connects the two aromatic subunits into an amide, urea and carbamate linkage. In certain embodiments, the acyclic linkage between the heterocyclic subunits may be transformed into, for example, a 3,5-disubstituted-1-H-pyrazole or a 2,5-disubstituted-1-H-imidazole linker to decrease the conformational flexibility of the molecules while retaining pharmacophore features.

In certain embodiment, inhibitor 4 may, for example, be modified by (a) placing appendages onto the quinoline and/or carbazole rings and the linker to occupy open space in the binding pocket (see FIG. 1); (b) changing the hydrazone linkage with acyclic and cyclic alternatives; and/or (c) enhance solubility and logP properties and block sites on the molecules that are likely to be metabolically active. In certain embodiments, the molecular weight of the compounds is <500 Da. In certain embodiments, the compounds do not include chirality. Thus, in certain embodiments, the compounds may have a structure of:

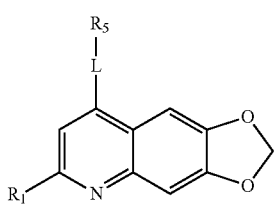

wherein $R_1$ is H, optionally substituted alkyl, optionally substituted cycloalkyl, optionally substituted aryl, cyano, optionally substituted heterocyclic, halogen, optionally substituted alkoxy, optionally substituted amino, or optionally substituted cycloalkoxy;

L is linking group; and
$R_5$ is selected from:

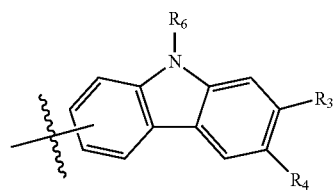

wherein $R_3$ and $R_4$ are each independently selected from H, optionally substituted alkyl, optionally substituted cycloalkyl, optionally substituted aryl, optionally substituted heterocyclic, optionally substituted alkoxy, halogen, or optionally substituted aryloxy; and $R_6$ is H, optionally substituted alkyl, optionally substituted cycloalkyl, optionally substituted aryl, optionally substituted alkoxy, optionally substituted cycloalkoxy, optionally substituted amino, or optionally substituted aryloxy; provided that at least one of the following substitutions is present:
(i) $R_1$ is optionally substituted alkyl or halogen;
(ii) $R_6$ is methyl; and/or
(iii) $R_3$ and $R_4$ are each independently selected from optionally substituted alkyl, optionally substituted cycloalkyl, optionally substituted aryl, optionally substituted heterocyclic, optionally substituted alkoxy, halogen, or optionally substituted aryloxy.

In certain embodiments $R_3$ and $R_4$ are each independently —$OCH_3$, —$OCH_2OCH_3$, —$CF_3$, —Cl, —Br, morpholino, optionally substituted alkoxy, optionally substituted cycloalkoxy, or optionally substituted aryloxy.

In certain embodiments, $R_6$ is C1-C5 alkyl, hydroxyalkyl (e.g., hydroxy(C1-C5) alkyl), alkoxyalkyl (e.g. C1-C5 alkoxy(C1-C5)alkyl), alkylamino (e.g. —NR'R" wherein at least one of R' and R" is C1-C5 alkyl), or aminoalkyl.

In certain embodiments $R_6$ is methyl or ethyl.

In certain embodiments, $R_1$ is C1-C5 alkyl, alkylamino, halogen, halogenated (C1-C5)alkyl, or hydroxy(C1-C5) alkyl.

In certain embodiments $R_1$ is methyl, trifluoromethyl, chloro, or bromo.

In certain embodiments, L includes at least one carbon/nitrogen bond. In certain embodiments, L may include an amide linkage, a carbamate linkage, a urea, an ether linkage, or an amino linkage. In certain embodiments, L is selected from —C(R$_2$)=N—NH—, —N=C(R$_2$)—NH—, =CH—N=C(R$_2$)—NH—, or

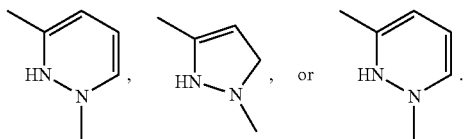

Illustrative inhibitors include:

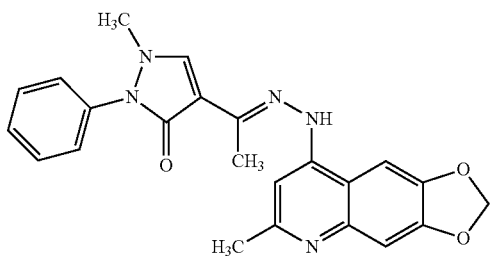

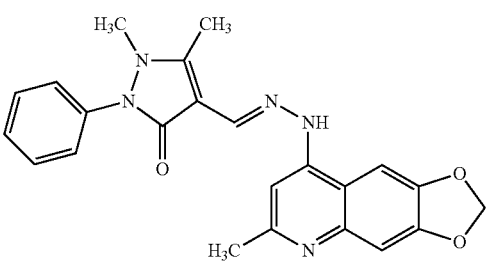

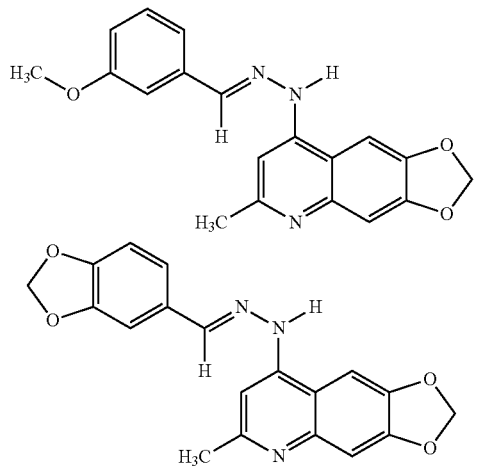

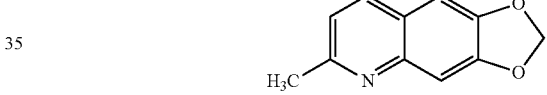

The compounds may be synthesized, for example, according to the illustrative scheme shown below, but it is understood that other synthesis schemes may be employed.

The two heterocyclic subunits, which can be individually modified via existing pathways, are condensed to afford a stable hydrazine linkage:

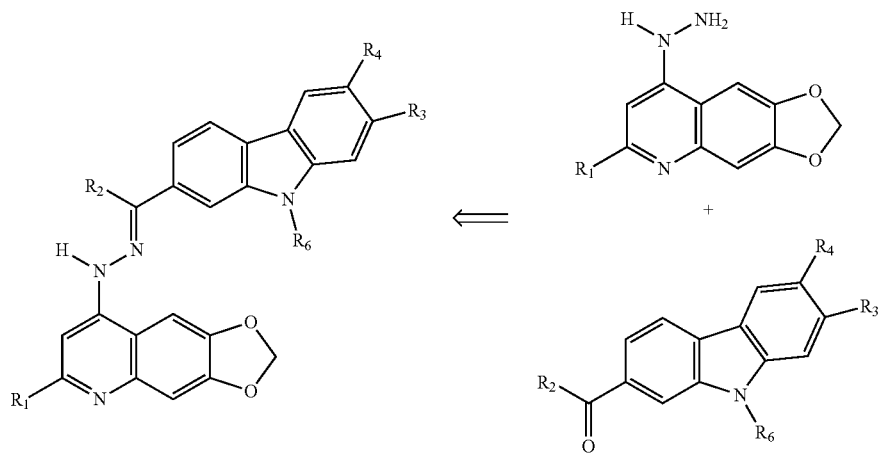

The synthesis of the 6,7-methylenedioxy-4-aminoquinoline and 9-substituted-9H-carbazole subunits is shown below:

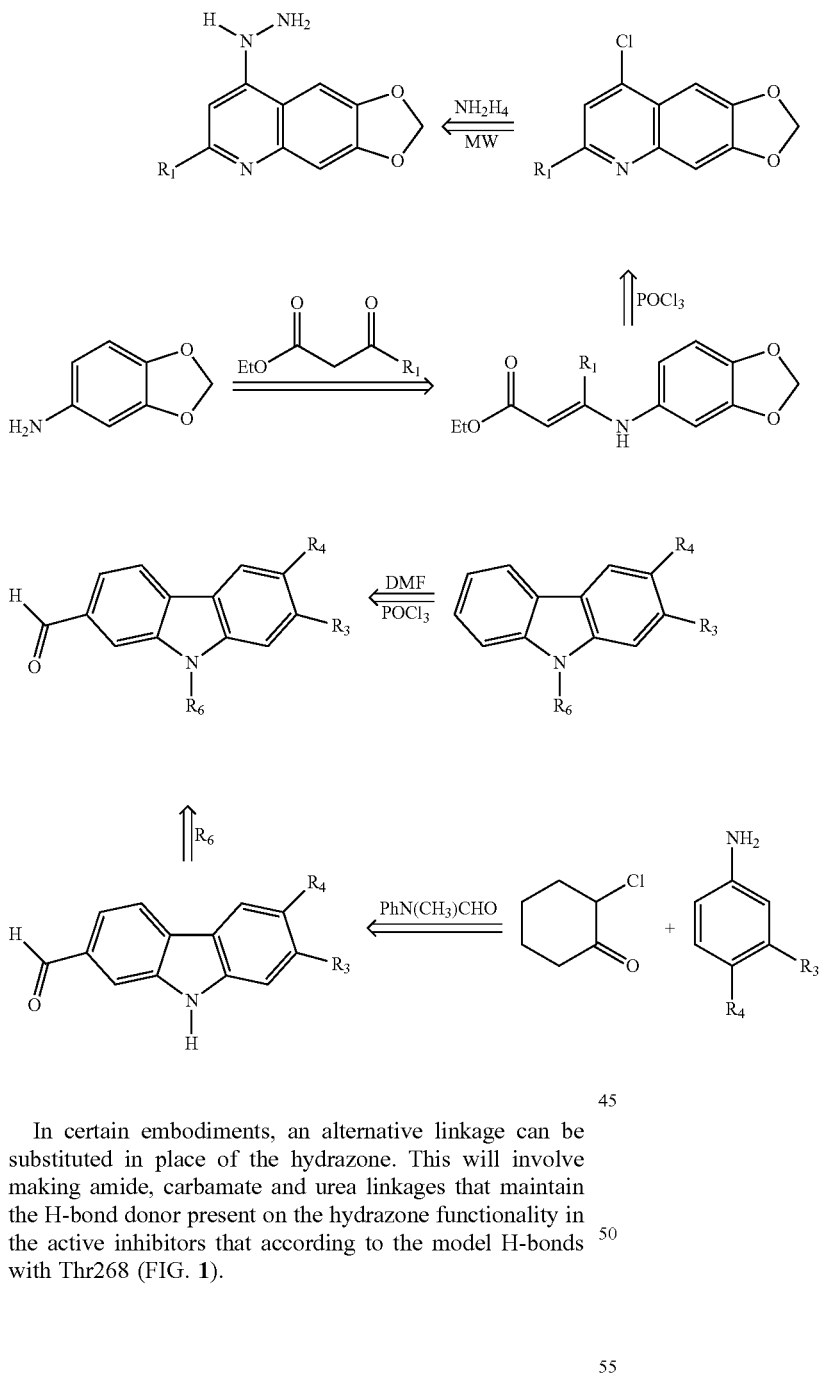

In certain embodiments, an alternative linkage can be substituted in place of the hydrazone. This will involve making amide, carbamate and urea linkages that maintain the H-bond donor present on the hydrazone functionality in the active inhibitors that according to the model H-bonds with Thr268 (FIG. 1).

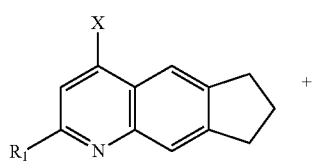

+

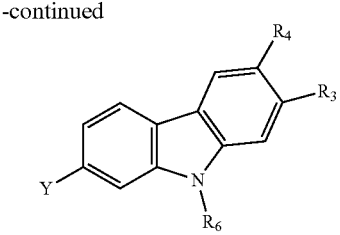

-continued wherein X is —NH$_2$ and Y is —C(O)Cl for an amide linkage; X is —N=C=O and Y is —OH for a carbamate linkage; and X is —N=C=O and Y is —NH$_2$ for a urea linkage.

In certain embodiments, the acyclic linkage between the quinoline and carbazole subunits may be replaced with a 3,5-disubstituted-1-H-pyrazole or a 2,5-disubstituted-1-H-imidazole linker. This substitution may remove some conformational flexibility, and possibly reduce the entropic penalty for binding, and eliminate the potentially deleterious hydrazone functionality. However, there are examples of drugs that contain a hydrazine functionality. The syntheses of the pyrazole and imidazole compounds are shown below.
In the design of these compounds, the H-bond donor on the N4-amino group of the quinoline is maintained.
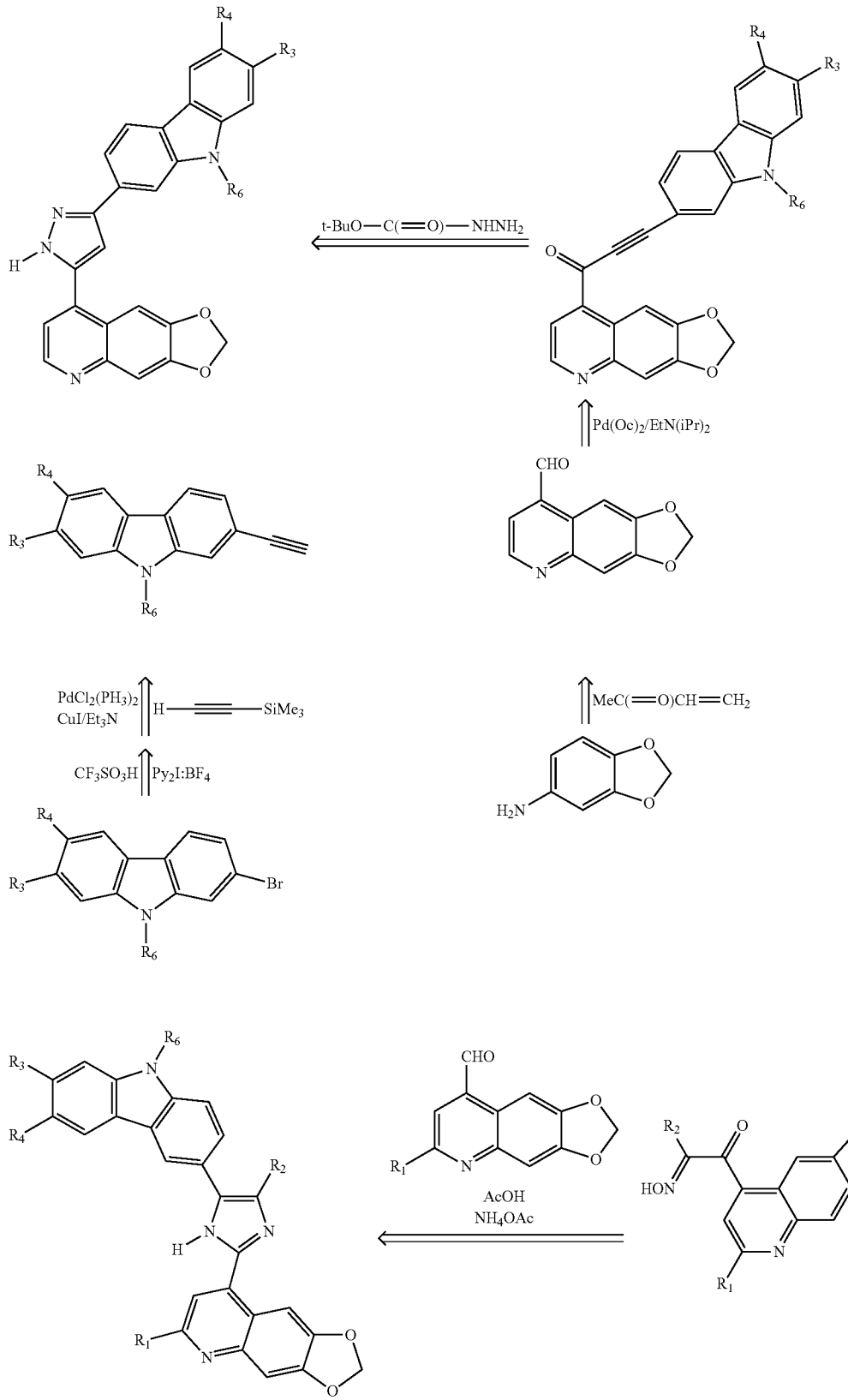

-continued

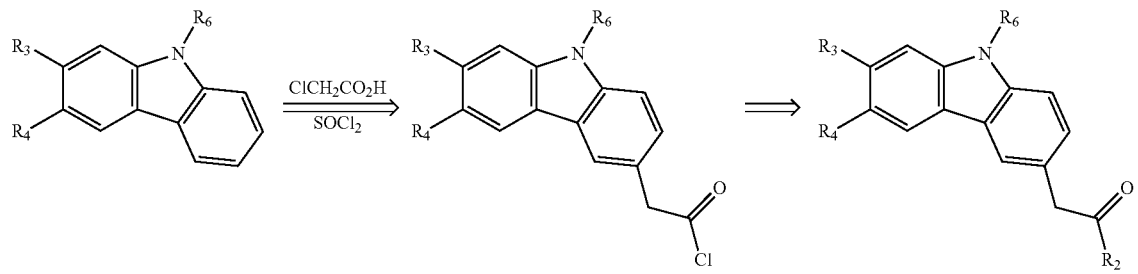

The inhibitory activity of the compounds may be sequentially evaluated using a molecular beacon, an excision assay and in vitro binding evaluated by ITC. The toxicity (MTT and clonogenic assays) and inhibition (activity in cell lysates) hAPE1 induced by the inhibitors may be screened in T98G cells.

Methods of Use

From a therapeutic standpoint, the compounds hereof may, for example, be exploited to overcome the resistance of some tumor cells to DNA damaging agents that results from overexpression of base excision repair pathway proteins. The classes of compounds hereof, which inhibit APE1 activity in vitro and in cells, may, for example, potentiate the toxicity of, for example, a methylating agent that selectively generates 3-methyladenine (3-mA), which is a substrate for human alkyladenine-DNA glycosylase (hAAG) and base excision repair.

In certain embodiments, the combination therapy disclosed herein may exhibit a synergistic effect in enhancing the efficacy of an anticancer agent. The synergistic effect of the combination therapy may also enable lower dosage levels of the anticancer agents at more frequent, periodic doses ("metronomic dosing"). This serves to decrease both costs and side effects, and also provides the option to use metronomic dosing to prevent cancer recurrence. Alternatively, a higher level of anti-tumor effects can be achieved by using anticancer agent MTD dosing levels. All of the advantageous dosing scenarios are the product of the larger therapeutic window enabled by combination therapy described herein and will benefit cancer patients through improvements in survival and quality of life.

The combination therapy disclosed herein may be useful for treating any type of neoplasm (e.g., cancer). Neoplasms treatable by the presently disclosed compounds include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcoma broadly includes tumors whose cells are embedded in a fibrillar or homogeneous substance like embryonic connective tissue.

A solid tumor can be malignant, e.g. tending to metastasize and being life threatening, or benign. Examples of solid tumors that can be treated include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

Illustrative cancers also include blood-borne cancers such as leukemia, myeloma, or lymphoma.

Moreover, tumors comprising dysproliferative changes (such as metaplasias and dysplasias) are treated or prevented in epithelial tissues such as those in the cervix, esophagus, and lung. Thus, the presently disclosed methods provide for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

In certain embodiments, the presently disclosed methods are directed to a method for inhibiting cancer growth, including processes of cellular proliferation, invasiveness, and metastasis in biological systems. Preferably, the method is employed to inhibit or reduce cancer cell proliferation, invasiveness, metastasis, or tumor incidence in living animals, such as mammals.

Also provided herein is a method of inducing cytotoxicity (cell killing) in cancer cells or reducing the viability of cancer cells. For example, the combination therapy can be used to induce cytotoxicity in cells of carcinomas of the prostate, breast, ovary, testis, lung, colon, or pancreas.

The combination therapy is particularly effective for administering to subjects having a cancer that over-expresses APE1 and/or involves the base excision repair (BER) pathway. In certain embodiments, a subject is identified as having a cancer that may be responsive to an hAPE1 inhibitor, and the combination therapy disclosed herein is administered to the identified subject. To determine susceptibility to the combination therapy, cancers from patients could be biopsied, grown in culture and subjected to the combination therapy. For example, APE1 activity has been used as a biomarker (Gossage et al, Base excision repair factors are promising prognostic and predictive markers in cancer, Curr. Mol. Pharmacol. 5, 115-124 (2012)). The molecular beacon test for APE1 activity described herein also may be a useful clinical screen. Illustrative cancers include prostate, ovarian, cervical, germ cell tumor, rhabdomyosarcoma, and colon (Evans et al, 2000. Going Ape over Ref-1 Mutat. Res. 461(2), 83-108).

In certain embodiments, the APE1 inhibitors disclosed herein may be used as the sole anticancer agent for treating a particular cancer. For example, the APE1 inhibitors exhibit selective toxicity against leukemia.

In certain embodiments, the APE1 inhibitors disclosed herein may be co-administered with an anticancer agent as part of a combination therapy. For example, the anticancer agent may be a DNA alkylating agent. Illustrative DNA alkylating agents includes a nitrogen mustard (e.g., mechlorethamine, cyclophosphamide, melphalan, chlorambucil), an alkyl sulfonate (e.g., busulfan), a nitrosourea (e.g., carmustine and lomustine), a triazine (e.g., dacarbazine and temozolomide), a platinum drug (e.g., carboplatin and cisplatin), and combinations thereof. In other embodiments, the anticancer agent may be a DNA cleaving agent such as bleomycin. In further embodiments, the anticancer agent may be a DNA oxidizing agent that directly or indirectly generates lesions for base excision repair such as an anthracycline (e.g., daunorubicin, doxorubicin, epirubicin). In further embodiments, the anticancer agent may be a recombination agent (e.g., trastuzumab). In additional embodiments, the anticancer agent may be a kinase inhibitor (e.g, vemurafenib), a cell cycle inhibitor, or a poly ADP ribose polymerase (PARP) inhibitor.

Compositions

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

Certain embodiments are described below in the following numbered paragraphs:

1. A method of inhibiting AP endonuclease-1/redox factor-1 (hAPE1) activity comprising application of a compound having the structure

wherein domain A has the structure

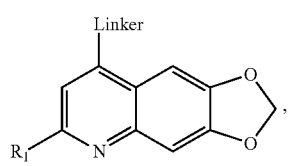

wherein $R_1$ H, a C1-C5 alkyl group, which can be branched, unbranched, cyclic or acyclic, or a 3-5 member ring, which can be homocyclic or heterocyclic;

the linker is a flexible or rigid linking group; and domain B includes a portion that is suitable to form a π-cation interaction with Arg177.

2. The method of paragraph 1 wherein the compound has the structure:

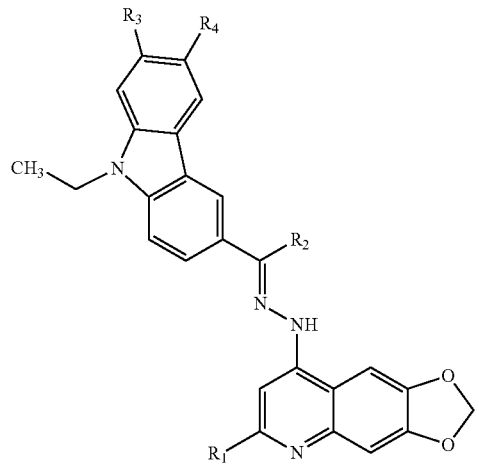

wherein $R_2$ is H, or a C1-C5 branched, unbranched, cyclic or acyclic alkyl group, and $R_3$ and $R_4$ are independently and separately a C1-C5 alkyl group, which can be branched, unbranched, cyclic or acyclic, or a 3-5 member ring, which can be homocyclic or heterocyclic.

3. The method of paragraph 1 wherein the compound has the structure:

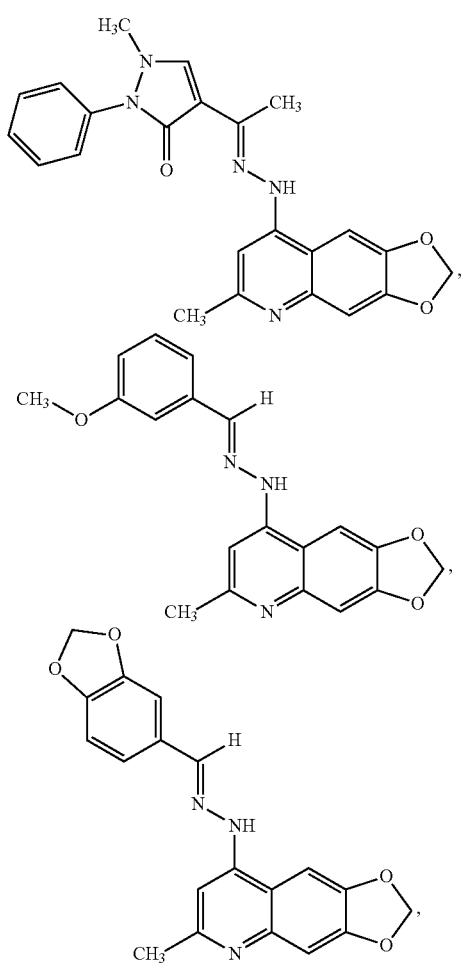

37

-continued

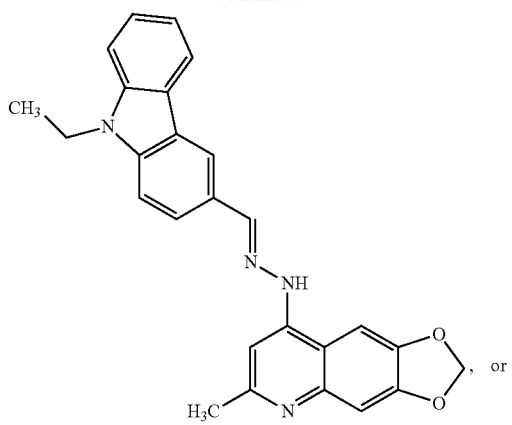, or

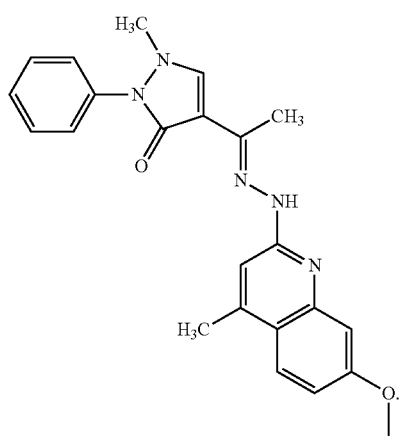 [SMILES: COc1ccc2c(C)cc(N/N=C(\C)c3cn(C)n(-c4ccccc4)c3=O)nc2c1]

4. A method of inhibiting AP endonuclease-1/redox factor-1 (hAPE1) activity comprising application of a compound having the structure

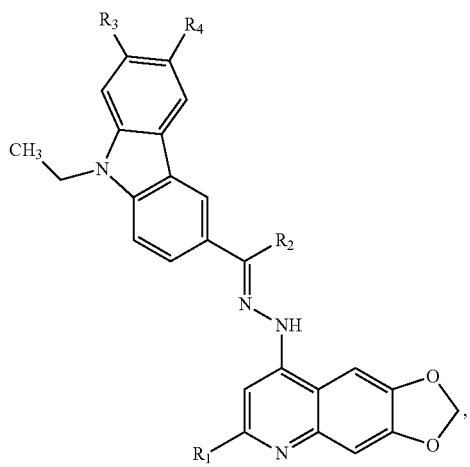

38

-continued

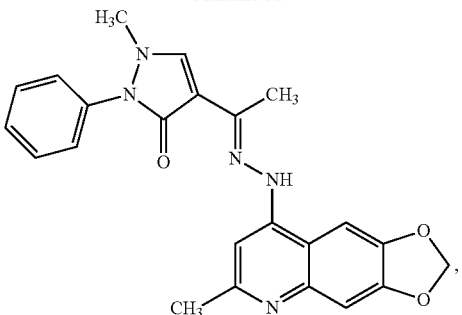,

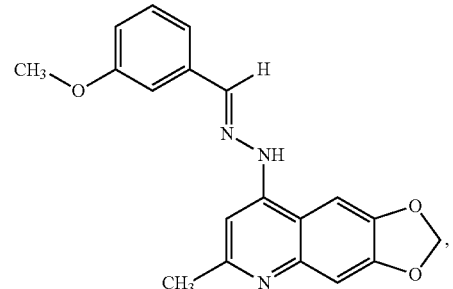,

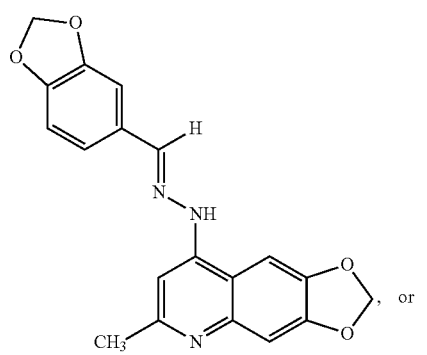, or

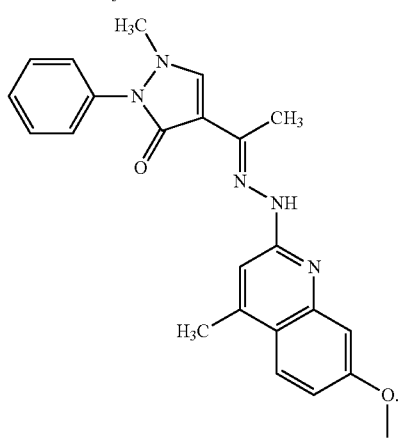

wherein $R_1$ H, a C1-C5 alkyl group, which can be branched, unbranched, cyclic or acyclic, or a 3-5 member ring, which can be homocyclic or heterocyclic; $R_2$ is H, or a C1-C5 branched, unbranched, cyclic or acyclic alkyl group; and $R_3$ and $R_4$ are independently and separately a C1-C5 alkyl group, which can be branched, unbranched, cyclic or acyclic, or a 3-5 member ring, which can homocyclic or heterocyclic.

5. The method of paragraph 4 wherein the compound has the structure:

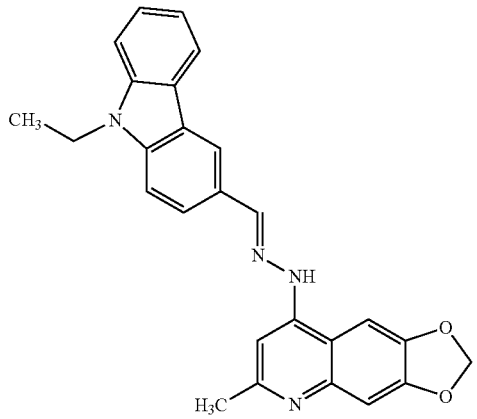 [SMILES: CCn1c2ccccc2c2cc(/C=N/Nc3cc(C)nc4cc5c(cc34)OCO5)ccc21]

6. A compound having the structure:

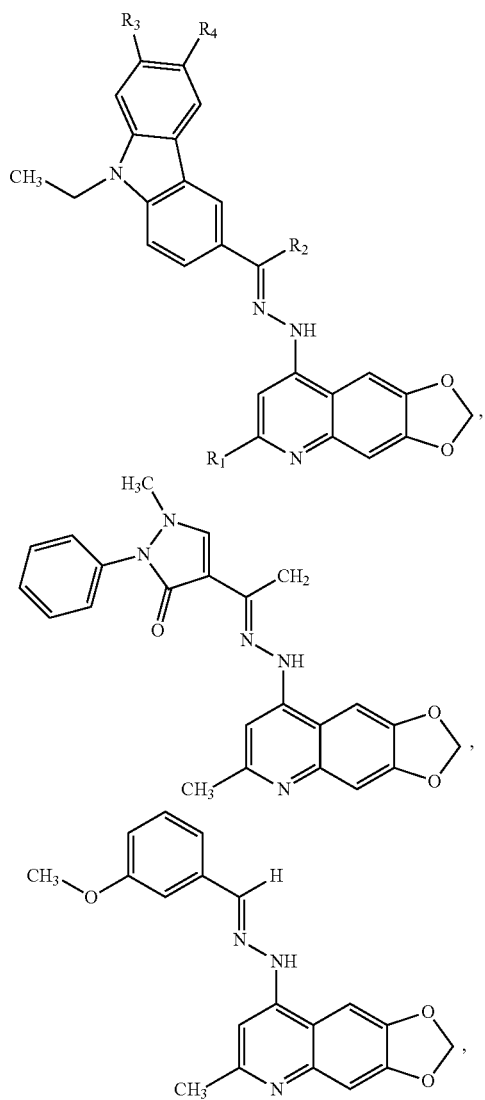

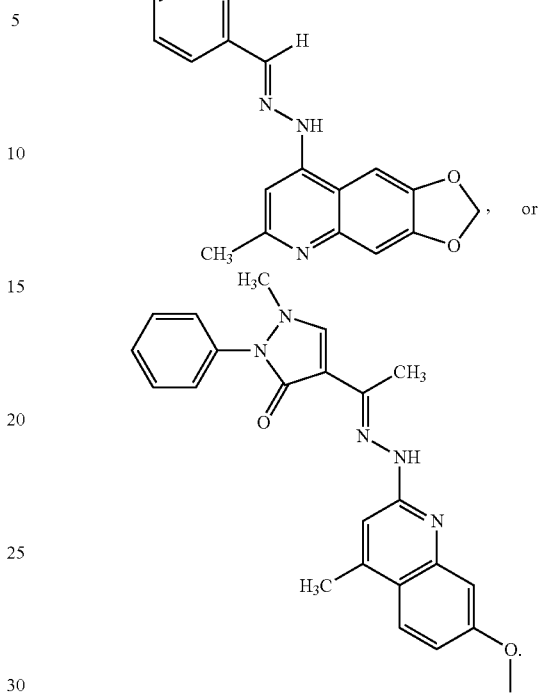

wherein $R_1$ H, a C1-C5 alkyl group, which can be branched, unbranched, cyclic or acyclic, or a 3-5 member ring, which can homocyclic or heterocyclic; $R_2$ is H, or a C1-C5 branched, unbranched, cyclic or acyclic alkyl group; and $R_3$ and $R_4$ are independently and separately a C1-C5 alkyl group, which can be branched, unbranched, cyclic or acyclic, or a 3-5 member ring, which can homocyclic or heterocyclic.

7. The compound of paragraph 6 wherein the compound has the structure:

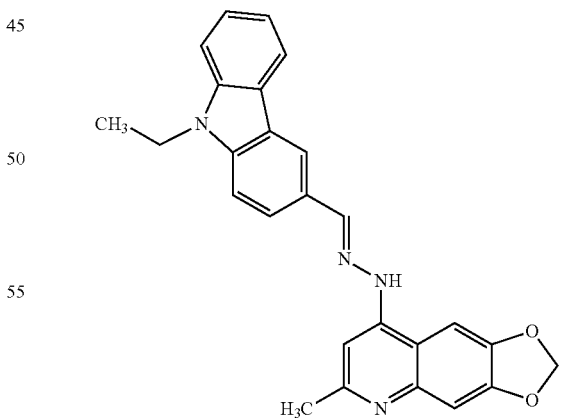

EXAMPLES

Figure 1D:
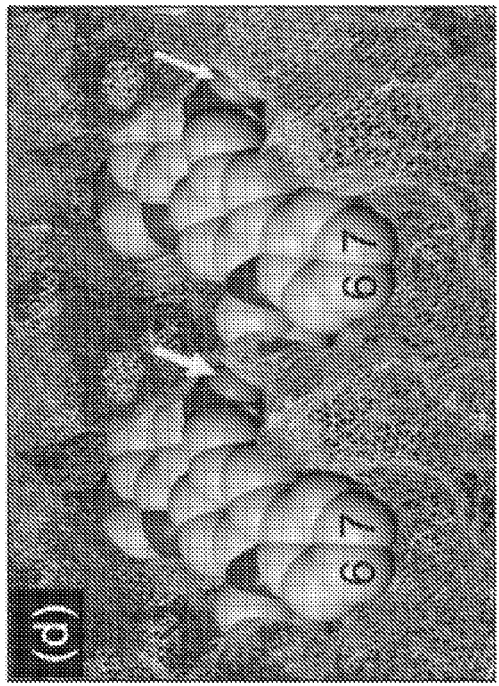
Figure 1A:
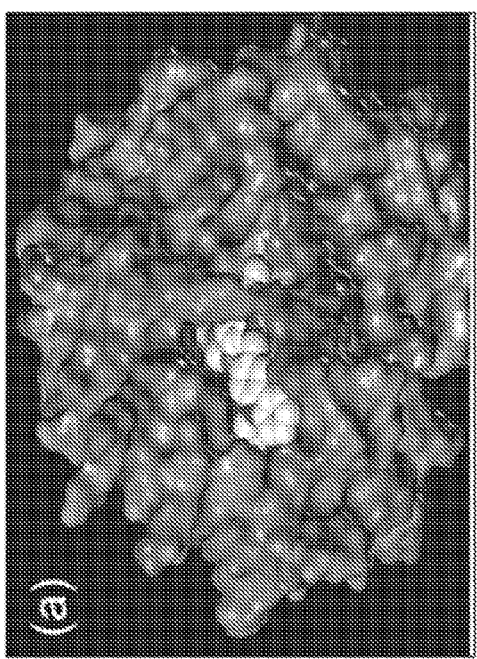
Figure 1B:
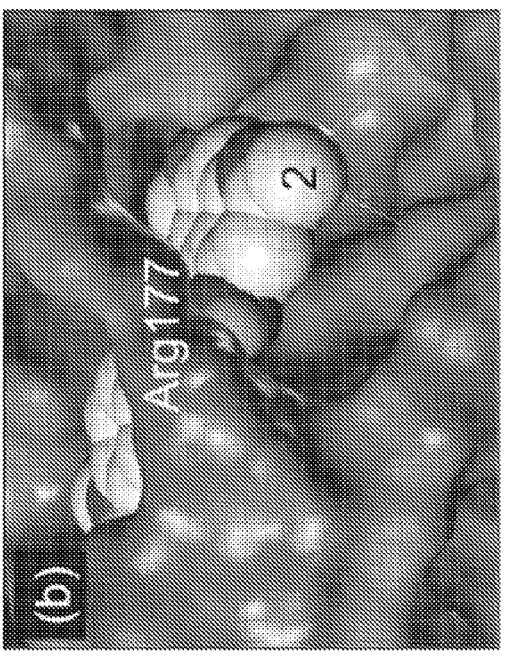

Modeling the Active Site-Rather than performing a random screen using a large commercial library, an in silico design and virtual screening was employed based on the X-ray crystallographic data of APE (1DEW.pdb; incorporated herein by reference (Mol et al, Nature 403, 451-456)), using the FlexX-Pharm Docking/CScore docking approach/CScore algorithms. It is important to note the similarity in the structure of the free protein and that in the protein-DNA complex with an AP site. The major exception is Arg177 that moves in from the major groove into the hole left by the AP site when it flips into APE1's active site. Using this approach, several new nM to uM APE1 inhibitors were identified and experimentally validated. An example of the most active inhibitor, compound 4 modeled with APE1 is shown in FIG. 1. The same Arg177 mentioned above, which is flexible, is predicted to move into a position similar to that in the APE1-DNA complex and stack on the carbazole ring of compound 4. This would allow it to make a strong t-cation interaction (FIG. 1b). Asn229 is within 3 Å of one of the oxygens in the methylenedioxy ring and Thr268 amide carbonyl can make an H-bond with the H—N on the hydrazone linker (FIG. 1d). The model indicates that the 2-methyl group on the quinoline ring can be enlarged (FIG. 1b) and that hydrophobic substitutions on the 6- and/or 7-positions of the carbazole would fill the remaining vacancy in the binding pocket (FIG. 1d).

Figure 2A:
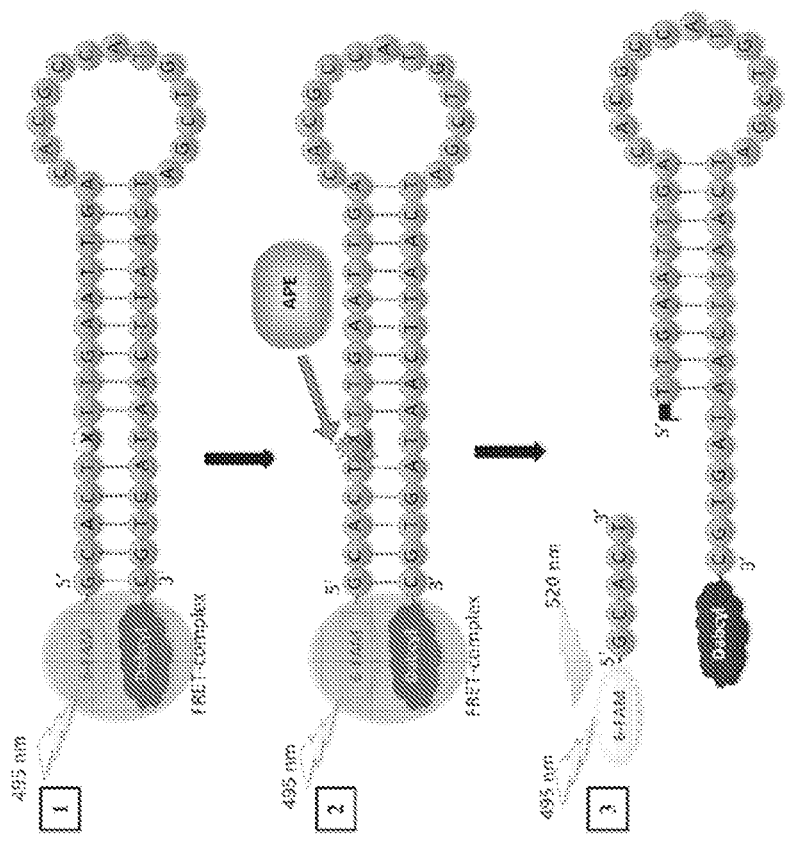
FIG. 2(a)-(d). Screen for inhibitors of APE1 activity: (a) the molecular beacon used to measure excision rate at the AP site in the absence and presence of inhibitor 4; (b) fluorescence change as a function of time with a specific inhibitor concentrations; (c) inhibition curve for inhibitor 4 (Ki=345 nM); (d) excision assay measuring the amount and type of cleavage produced by APE1 in the absence and presence of increasing concentrations of Inhibitor-1.
Figure 2B:
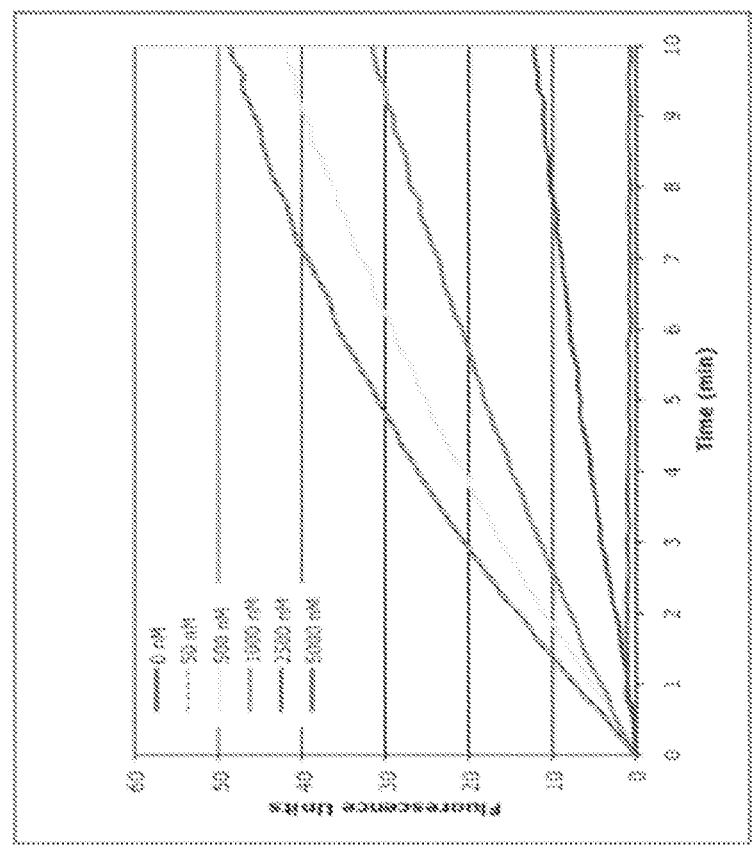
Figures 2C, 2D:
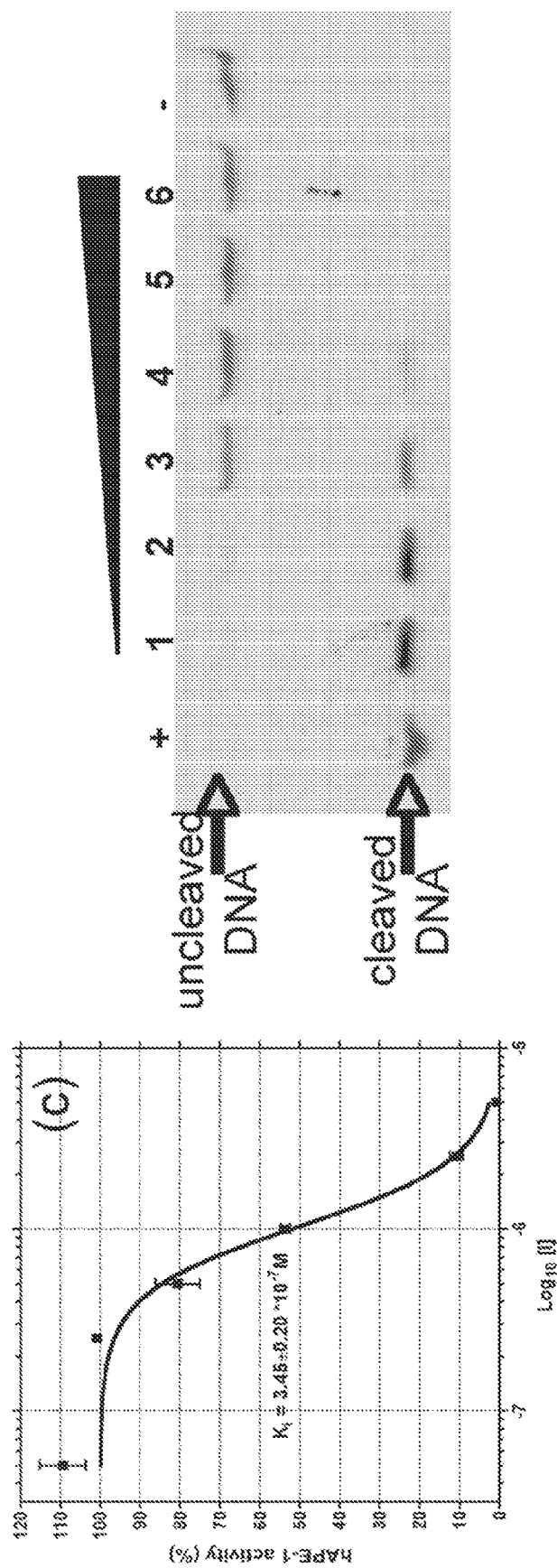

Screening Assays for APE1 Inhibition—The initial screen was designed to look at the effect of potential inhibitors on APE1 repair kinetics. The approach can be used as a high throughput screen by choosing a specific timepoint to monitor. The screen utilizes a molecular beacon with a tetrahydrofuran (THF) abasic site within the stem region of a DNA hairpin that has a fluorophore on the 5'-terminus and a quencher on the 3'-terminus (FIG. 2a). Compounds that had good inhibitory activity in this screen were then retested using a gel based assay to directly measure DNA excision as a function of inhibitor concentration. An example of the molecular beacon screen and the excision assay are shown in FIGS. 2b,c and 2d, respectively.

Evidence that Inhibitor Binds Directly to APE1—Evidence that the inhibitors directly bound to APE1 was established using isothermal titration calorimetry (ITC). This method provides thermodynamic information on the binding affinity, stoichiometry and the thermodynamic parameters, i.e., $\Delta G$, $\Delta H$ and $T\Delta S$. In addition to the studies on the binding of the inhibitor to APE1, it was also confirmed that the inhibitor did not block enzymatic activity by binding to the DNA.

Figure 3A:
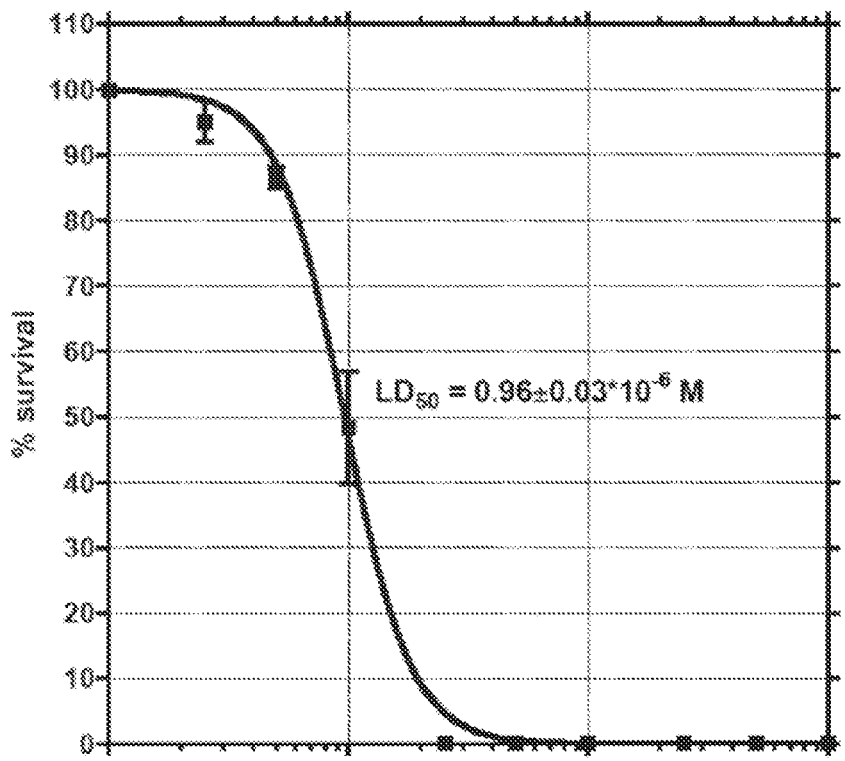
FIGS. 3(a)-(b). (a) Toxicity of Inhibitor-1 evaluated using MTT assay in T98G cells (LD50=960 nM). (b) Toxicity of MeLex (efficiently generates 3-mA) in the absence (o) and presence of 50 nM ( ) or 250 nM (∇) inhibitor 4.

Toxicity of APE1 Inhibitors in T98G Glioma Cells—A short term (MTT assay) and long term (clonogenic assay) dose response toxicity for the inhibitors was performed in T98G glioma cells in the absence of a DNA alkylating agent. This cell line was selected because it is quite resistant to many DNA alkylating agents; therefore, it represents a good model to test the potential effect of APE1 inhibition on the toxicity of DNA damaging compounds. The results of this study are shown in FIG. 3a.

Figure 3B:
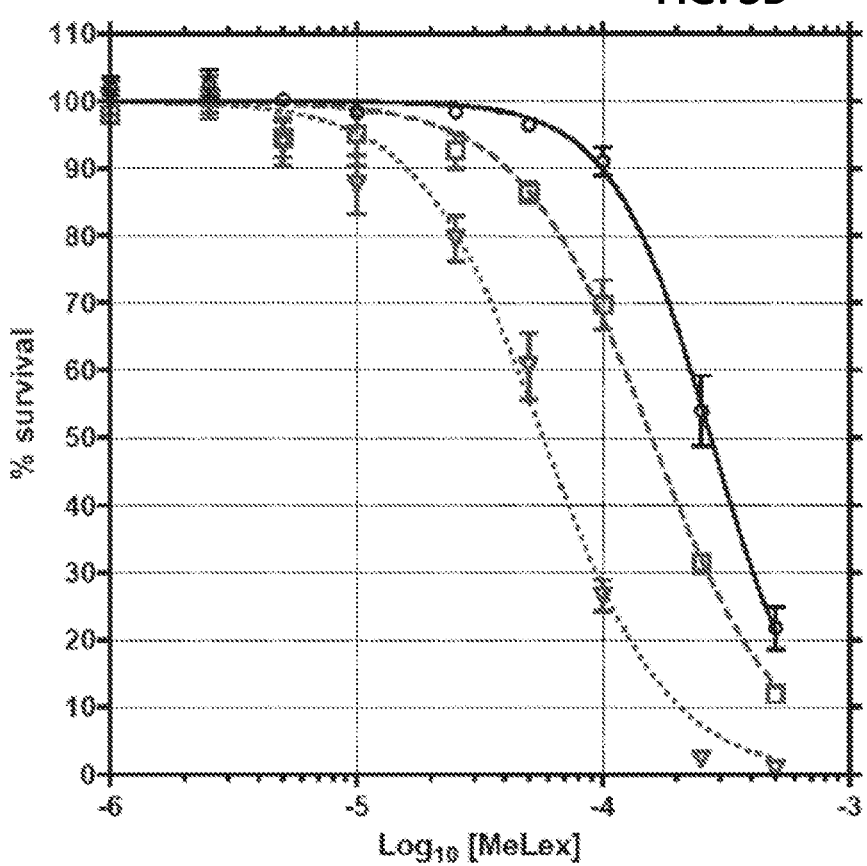

Effect of APE1 Inhibitors on the Toxicity of DNA Alkylating Agents—Concentration-dependent responses for the APE1 inhibitors on the toxicity of Me-lex were established in the T98G cell line. Me-lex was developed to selectively and efficiently generate N3-methyladenine (3-mA). It has been previously demonstrated that the toxicity of Me-lex, i.e., 3-mA, is dependent on BER. Using a range of Me-lex concentrations, tested 50 and 250 nM APE1 inhibitor were tested (FIG. 3b). The results show that the toxicity of Me-lex is significantly enhanced by the APE1 inhibitor. Note that the data have been corrected for the background toxicity of the APE1 inhibitors (FIG. 3b) so the graph show how the inhibitors enhance the toxicity of Me-lex. The results are consistent with inhibition of APE1 activity being responsible for the added toxicity of Me-lex.

Figure 4:
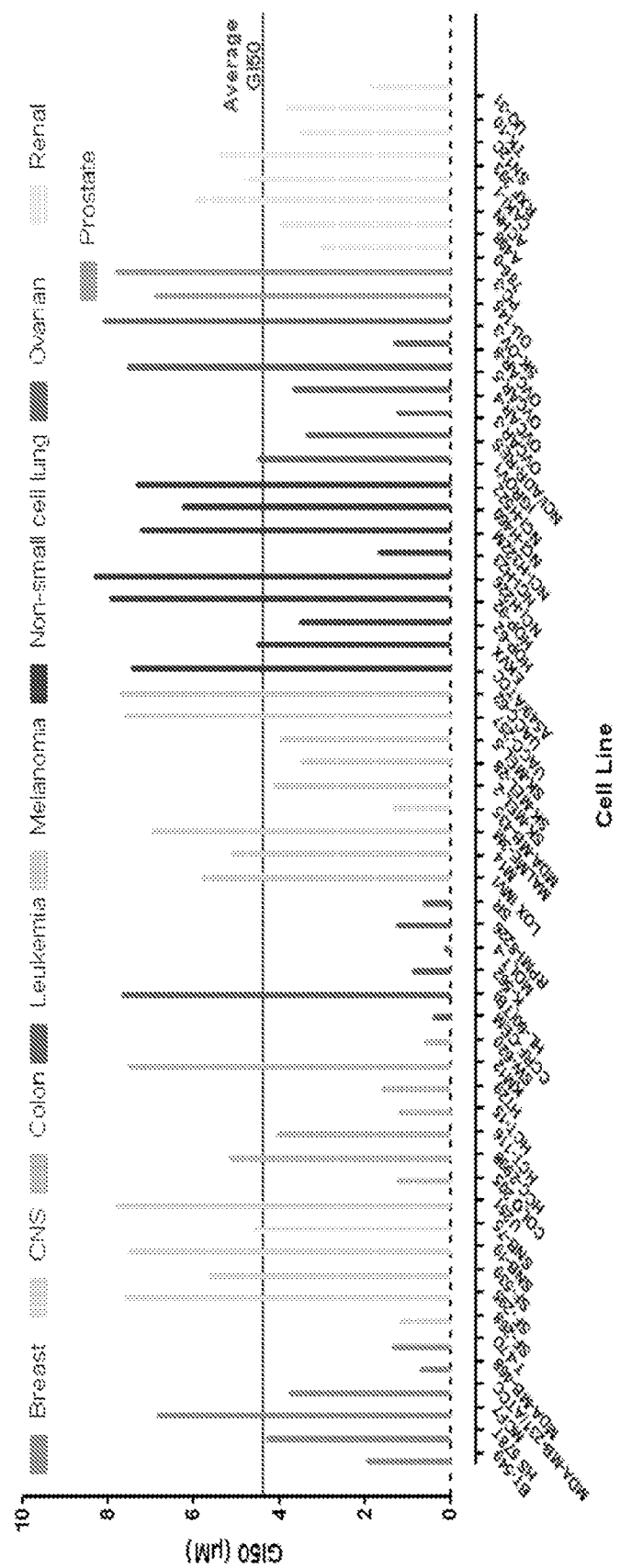
FIG. 4. Growth inhibition (GI$_{50}$) induced by 10, 1, 0.1, 0.01, 0.001 μM AP inhibitor 4 (see Table 1 for structure) in the NCI 60 cell line.

APE1 Inhibitor 4 Selectively Inhibits Growth in Leukemia Cell Lines—To determine whether APE1 inhibitor 4 had any selectivity for specific tumor cell types, growth inhibition (GI) in the NCI panel of 60-cell lines was analyzed (FIG. 4). The average growth inhibition ($GI_{50}$) in all the lines was 4.4±2.6 µM. In 4 of the 6 leukemia cell lines, the $GI_{50}$'s were in the nM range with an overall average of 1.8±2.9 µM. However, if the HL-60 line is omitted, the $GI_{50}$ drops to 640±400 nM, with the MOLT-4 line having a $GI_{50}$ of 133 nM. In only 2 of the remaining 54 non-leukemia cell lines is the $GI_{50}$<1 µM. The origin of this selectivity for leukemia cells is unclear; the mutations present in the sensitive and insensitive lines do not provide any insight. MeLex was tested in the same NCI cell lines and the most sensitive ($GI_{50}$ of 900 nM, data not shown) was CCRF—CEM, a p53 mutant acute lymphoblastic leukemia cell line.

Figure 5:
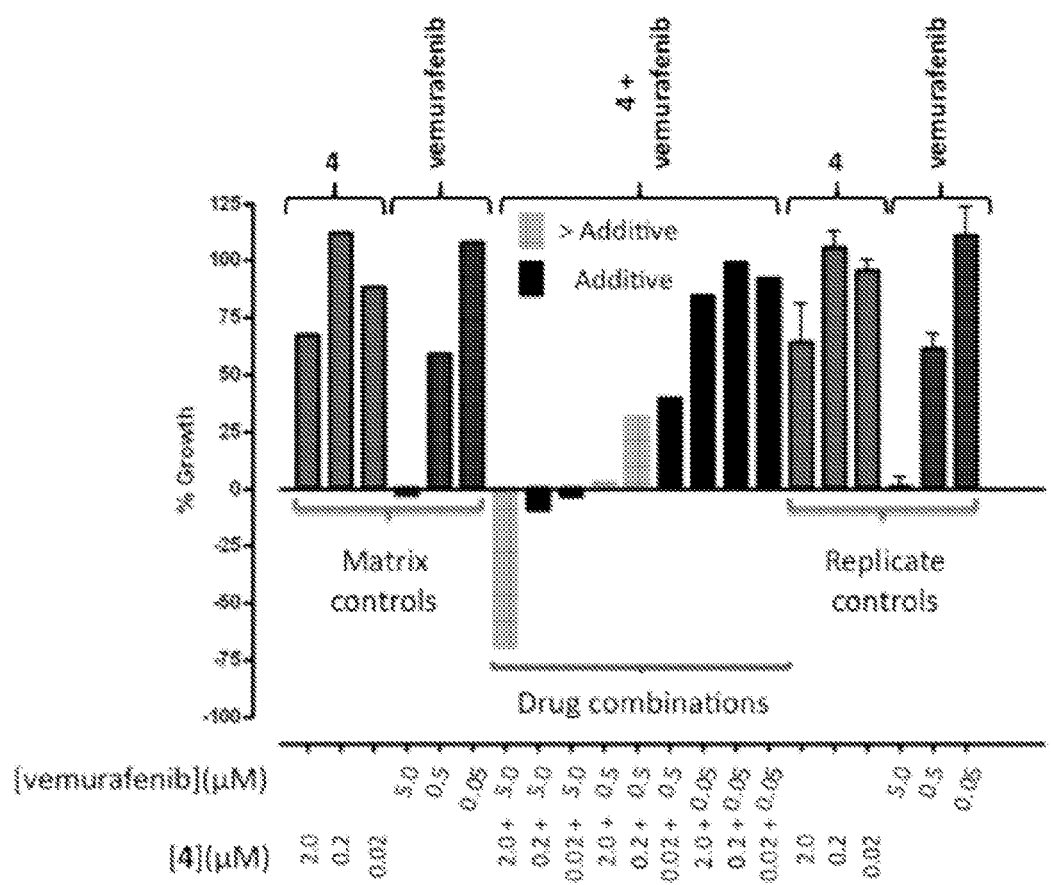
FIG. 5. An example of the enhanced activity of vemurafenib in combination with APE1 inhibitor 4 in SK-MEL-5 melanoma cells. Matric controls are run in singlet on each matrix and compared to replicate (n=10) controls for vemurafenib and 4. The combination of the 2 compounds at different combinations are shown: green bar (>additive) means that the combination of compounds enhanced toxicity by >3 S.D. from the combined mean of individual compounds.
Figure 6A:
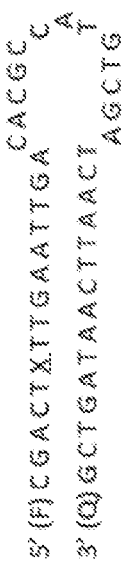
FIG. 6. Inhibition of APE-1 endonuclease activity by 1-5,8,28-30, E3330 and EtBr in the molecular beacon assay (K$_1$ values determined from this assay were calculated as described in Experimental Procedures and are shown in Table 1). (A) Sequence of THF modified hairpin DNA substrate, where, F, fluorophore and Q, quencher. (B-D) Changes in APE-1 endonuclease activity as a function of varying concentrations of potential APE-1 inhibitor molecules: (B) 1(Δ) 2 (□), 3 (○), 4 (◇); (C) 5 (Δ), 6 (□), EtBr (▼), E3330 (X); (D) 7 (○) 8 (◇); and (E) 28 (■), 29 (●) and 30 (▲).
Figure 6B:
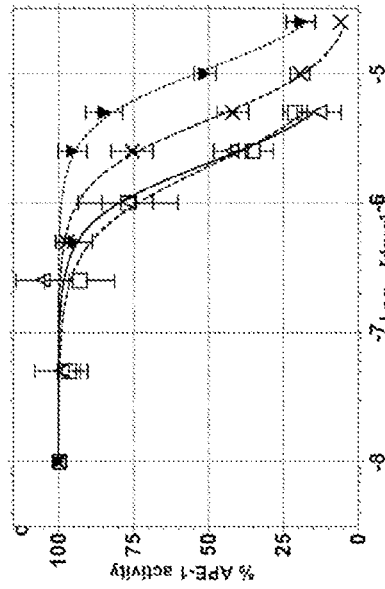
Figure 6C:
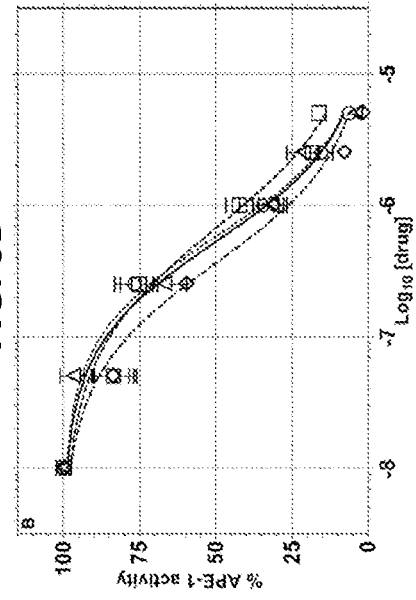
Figure 6D:
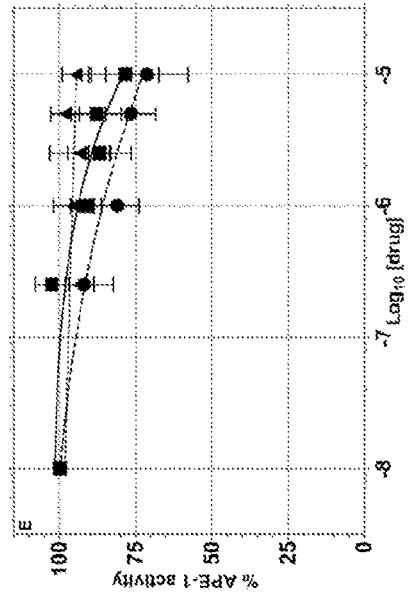
Figure 6E:
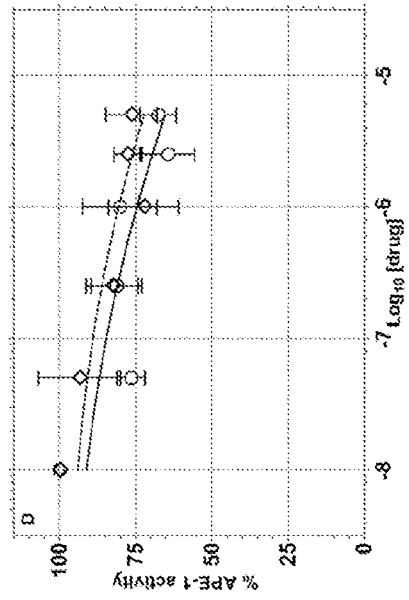

APE1 Inhibitor 4 Enhances the Toxicity of Anticancer Drugs in the NCl60 Cell Line Assay—In a preliminary screen using 10 randomly selected cell lines, the effect of APE1 inhibitor 4 on the growth of 20 recently approved non-genotoxic anticancer drugs was assayed. Several examples of >additive responses were observed, with one example shown in FIG. 5. The responsive cell is a SK-MEL-5 (melanoma) line and the >additive effect was observed with Vemurafenib (Zelboraf), a 1st-in-class B-Raf kinase inhibitor selective for melanomas with a V600E mutation. There is no structural similarity between 4 and Vemurafenib, and 4 alone was not particularly toxic ($GI_{50}$, 4 µM) in the SK-MEL-5 line (FIG. 4).

In summary, novel nM APE1 inhibitors have been identified based upon molecular modeling and in vitro screening. The molecules bind to the APE1 protein but not to the DNA. The strong enhancing effect of the inhibitors on the toxicity of a DNA methylating agent has been confirmed in a cell line that is resistant to alkylating agents.

Experimental Procedures

Materials. Potential APE-1 inhibitor compounds were obtained via the Developmental Therapeutics Program of the National Cancer Institute, National Institute of Health, Bethesda, Md. Chemicals, solvents and CelLytic NuCLEAR Extraction kit were purchased from Sigma Aldrich Chemicals (St. Louis, Mo.). Oligonucleotide sequences were custom-synthesized by Integrated DNA Technologies (Coralville, Iowa) or Sigma Aldrich (St. Louis, Mo.). Nickel nitrilotriacetate (Ni-NTA) sepharose resin was procured from Qiagen Inc. (Valencia, Calif.). pENTR, pDEST17, *Escherichia coli* DH5a, pre-cast polyacrylamide gels, DNAzol reagent, cell culture components and CyQUANT Cell Proliferation Assay Kit were obtained from Invitrogen (Carlsbad, Calif.). Human glioblastoma (T98G) cells were obtained from American Type Culture Collection (ATCC) (Manassas, Va.). CellTiter 96 AQueous One Solution Reagent was obtained from Promega Corp, Madison, Wis. DNA Damage Quantification kit (abasic site counting) was obtained from Dojindo Molecular Technologies (Rockville, Md.). *Escherichia coli* C41(DE3) cells were obtained from Lucigen Corp. (Middleton, Wis.). His-Pur Cobalt resin, Trypan Blue stain, BCA Protein assay kit, dialysis cassettes and molecular biology grade buffers, as well as plastic- and glass-ware were obtained from Fisher Scientific (Pittsburgh, Pa.). The sequence-specific alkylating agent, 1-methyl-4-[1-methyl-4-(3-methoxysulfonylpropanamido)pyrrole-2-carboxamido]pyrrole-2-carboxamido}propane (MeLex) was synthesized as previously described. Zhang et al., Biochemistry 32, 7954-7965 (1993).

Virtual Screening Strategy for Small-Molecule Inhibitors of APE-1. The 3D structural model of APE-1 was constructed based on the X-ray crystallographic data for 1DEW in the PDB (Mol et al. nature 403, 451-456 (2000)), incorporated herein by reference, and was further modeled by refining the low-resolution region using our previously reported protocols. Xie et al, Proteins: Struct, Funct., Genet. 53, 307-319 (2003). All computations were performed using Sybyl 8.2 (Tripos Associates) on a Dell 32 CPU Linux Cluster. After the generation of Surflex-Dock protomol using the reported binding residues and default parameters, a virtual docking screen was carried out on the reported 3D virtual chemical compound library. For each compound, 20 optimal conformers were generated by docking calculations. The conformer with the best total Hammerhead score (8.21) was chosen for further biochemical and cellular studies.

Cloning, Expression and Purification of APE-1. The coding sequence for the human apurinic endonuclease (ape-1) was previously amplified by Reverse Transcriptase-Polymerase Chain Reaction (RT-PCR) and cloned into pENTR, a directional TOPO-cloning Gateway entry vector (R. W. Sobol et al., unpublished). The ape-1 coding sequence was sub-cloned into the destination vector pDEST17 via the LR reaction, which introduced an N-terminal polyhistidine (6×) coding sequence. The pDEST17-ape-1 construct, amplified and purified from *Escherichia coli* DH5a cells was used to transform 'OverExpress' *E. coli* C41(DE3) cells for expression and purification of recombinant (H is)$_6$-APE-1 protein. Transformed *E. coli* C41(DE3) was grown overnight at 37° C. and constant shaking (100 rpm) in 5 mL Luria Bertani (LB) medium containing 100 μg mL$^{-1}$ ampicillin. The overnight culture was used to seed 500 mL LB medium and the cells were allowed to grow at 37° C. with constant shaking (100 rpm, 2 h) until the culture reached mid-log phase ($\lambda_{600\ nm}$~0.5). Isopropyl β-D-1-thiogalactopyranoside (IPTG) at 0.8 mM was used to induce APE-1 expression, at 25° C., under constant stirring (100 rpm, ~2 h). At 16 h post-induction, the cells were harvested by centrifugation (5000 rpm, 10 min), washed free of media with 1× phosphate buffered saline (PBS) and resuspended in 5.77 mM sodium phosphates (4.3 mM Na$_2$HPO$_4$+1.47 mM NaH$_2$PO$_4$, pH 7.4), 2.7 mM KCl, 330 mM NaCl, 10% (v/v) glycerol, 0.5% (v/v) Tween-20, 0.1% (w/v) lysozyme, 10 units mL$^{-1}$ Benzonase (nuclease), and incubated for 30 min at 25° C. Intact cells were lysed by ultrasonication (5 min, 30% amplitude), centrifuged at 10,000 rpm, for 30 min, and clear supernatant (cell lysates) collected. APE-1 protein in cell lysates was purified by immobilized metal affinity chromatography using Ni- or Co-chelated resins to bind them to the N-terminus His$_6$ tag. Immobilized APE-1 protein was eluted using a 10-250 mM gradient of imidazole in 10 mM HEPES (pH 7.4), 50 mM KCl. Pooled fractions containing APE-1 protein was dialyzed against 10 mM HEPES (pH 7.4), 250 mM KCl, 10% (v/v) glycerol and protein concentration estimated colorimetrically (BCA protein assay kit) as well as by UV absorbance ($\lambda_{280\ nm}$). Homogeneity of purified proteins was checked by sodium dodecyl sulfate-polyacrylamide gel electrophoresis (SDS-PAGE), followed by staining with 0.05% Coomassie Brilliant Blue R-250, 50% (v/v) methanol, 10% (v/v) acetic acid. Purified proteins were stored at −80° C. (long-term) or kept at −20° C. during regular use.

Molecular Beacon Assay for Screening of APE-1 Inhibitors. A fluorescence-based molecular beacon assay to measure APE-1 protein activity and inhibition was performed as described previously with some modifications. Tang et al. Neuro Oncol. 13, 471-486 (2011) APE-1 (2 nM) in 10 mM HEPES (pH 7.8) 0.5 mM MgCl, 100 mM NaCl, 100 mM KCl, 0.0005% (w/v) BSA, was incubated with 20 nM 5'-(F)-CGACTXTTGAATTGA CACGCCATGTCGATCAATTCAATAGTCG-(D)-3' [X=tetrahydrofuran (THF) abasic site modification; F, 6-carboxyfluorescein (6-FAM); and D, DABCYL] that forms a hairpin with a 15 base pair stem and a 13 base loop. The THF modification is a known substrate for APE-1 excision. APE-1 mediated cleavage of the phosphodiester backbone at the THF-abasic site led to release of the 5' 6-FAM (fluorophore) containing pentanucleotide, disrupting the Förster Resonance Energy Transfer (FRET) mediated quenching of the 6-FAM by DABCYL in the native hairpin oligomer. Since the signal was generated by continuous liberation of the fluorophore-labeled excision fragment, progress of this reaction could be monitored in real-time using a Cary Eclipse fluorescence spectrometer (Varian, Palo Alto, Calif.) or a Synergy H1 multi-well plate reader (BioTek, Winooski, Vt.). Reactions were optimized to yield ~90% substrate turnover in 10 min, and fluorescence intensities measured every 12 s at 495 nm excitation and 520 nm emission. Data from the first 1-3 min of the assays (linear phase) were used to determine rate of substrate turnover ($V_0$). The Michaelis constant ($K_M$) was deduced experimentally, by incubating 2 nM APE-1 protein with 2-500 nM hairpin DNA substrate and measuring $V_0$ —the experimentally observed $V_0$ were analyzed as a function of substrate concentration [S] via non-linear regression using Prism (v.4; GraphPad Software, Inc., La Jolla, Calif.) and the $K_M$ was calculated as per the algorithm in the software package. To assay inhibition, 2 nM APE-1 protein was pre-incubated with 0.05-10.00 μM of the candidate inhibitors at 25° C. for 60 min, before initiating the excision assay by addition of hairpin DNA substrate. $V_0$ was calculated at various concentrations of inhibitors and represented as inverse function of increasing inhibitor concentration [I]. Data were plotted on Prism and analyzed by non-linear regression to obtain values for inhibitor concentration at 50% inhibition (IC$_{50}$), and the inhibitory constant ($K_i$) was approximated by the formula, $K_i=[IC_{50}]/(1+[S]/K_M)$ is. All assays were carried out in three independent sets to obtain mean data and standard error of mean.

Gel-Based Assay for APE-1 Inhibitors. In addition to the real-time fluorescence assay for studying inhibition of APE-1 activity, a gel-based assay was also employed to visualize and quantify repair activity of APE-1 and its inhibition. Briefly, 20 nM APE-1, in 10 mM HEPES (pH 7.8) 0.5 mM MgCl$_2$, 100 mM NaCl, 100 mM KCl, 0.0005% (w/v) BSA, was incubated with 100 nM of a duplex DNA that was formed by annealing 5'-(F)-CGATCATCACTXT-TGAGACTGACACTGACC-3', which contained the THF abasic site modification (X), a 5' 6-FAM fluorophore (F), and the complementary sequence, 5'-GGTCAGTGTCA-GTCTCAATAGTGATGATCG-3'. Cleavage by APE-1 at the THF abasic site led to release of the 5'-fluorophore tagged 11-nucleotide fragment, which could be resolved from the uncleaved 30-nucleotide fragment (intact substrate) by gel electrophoresis under denaturing conditions. To assay inhibition of APE-1 activity, the APE-1 protein was pre-incubated with 5-100 μM of the candidate inhibitors for 60 min, before initiation of the excision assay by addition of duplex DNA substrate. Reaction products were separated on a 20% denaturing (urea) polyacrylamide gel, and the bands were visualized by fluorescence emission of the 6-FAM under ultraviolet illumination using a GelDoc EZ Imager (BioRad, Hercules, Calif.) and quantified using the Image Lab Software (BioRad, Hercules, Calif.). Inhibitory activity was calculated by co-relating fluorescence intensity of the 11-nucleotide fragment product as the (inverse) function of inhibitor concentration. All assays included a positive control (complete digestion of duplex DNA in absence of any inhibitor) as well as a negative control (uncleaved duplex DNA), which corresponded to 100% and 0% substrate turnover, respectively. Substrate turnover in presence of candidate inhibitors were calculated as percentage of positive control. Data were plotted on Prism, analyzed by non-linear regression and the $IC_{50}$ values were obtained from the dose response curves. All assays were carried out in three independent measurements.

Fluorescence and UV Spectrometry Binding Studies. The fluorescence spectra were measured at room temperature on a Cary Eclipse fluorescence spectrometer (Varian, Palo Alto, Calif.). The fluorescence properties of 1 and 4 were measured in 10 mM HEPES, 0.5 mM $MgCl_2$, 100 mM KCl, 100 mM NaCl, 2% glycerol, in absence or presence of wild type (unmodified) hairpin DNA (5'-CGAATTCGCAGGAC-CGAATTCG-3') or THF-modified hairpin DNA (5'-CGAXTTCGCAGGACCGAATTCG-3') or APE-1 protein. A solution of 0.5 µM of either DNA sequence was titrated against 1-10 µM ethidium bromide (EtBr) to determine saturation of EtBr by fluorescence (530 nm excitation with 610 nm emission) and the subsequent displacement of EtBr (4 µM) by 1-20 µM 1 or 4 was also assayed. The APE protein-inhibitor binding fluorescence was assayed by titrating 0.1-20 µM of 4 against 1 µM of APE-1 protein. Displacement of 4 (6 µM) from 1 µM APE-1 protein by increasing amounts (0.75-30 µM) of E3330 was also measured.

The effect of the small molecules on DNA stabilization was determined by measuring UV absorption of DNA at 260 nm as a function of temperature in a Cary 300 UV-visible spectrophotometer (Varian, Palo Alto, Calif.) under similar conditions as previously described. The transition temperatures ($T_M$) was calculated from the first derivative analysis.

Isolation and Assay of APE-1 Protein from Nuclear Extracts of Glioma Cells. Human glioblastoma cells (T98G) were maintained in growth medium, i.e., Eagle's Minimum Essential Medium (EMEM) with 10% fetal bovine serum (FBS), 50 µg $µL^{-1}$ gentamycin, 1×MEM non-essential amino acids and 1 mM sodium pyruvate. Cells were harvested by Trypsin-EDTA treatment, washed with 1×PBS and nuclear proteins isolated using the CelLytic NuCLEAR Extraction kit (Sigma-Aldrich) as per manufacturer's instructions. Isolated nuclear proteins were estimated colorimetrically (BCA protein assay) and stored at −80° C. (long term) or at −20° C. during regular use. To assay APE-1 activity in T98G cells, nuclear extracts were serially diluted in 10 mM HEPES, 50 mM KCl, 1 mM DTT, 20% (v/v) glycerol and the activities measured via the molecular beacon assay (as described above). The final dilution used for all assays ($EC_{2\,nM}$, effective concentration of 2 nM) gave ~90% turnover of 25 nM hairpin substrate DNA in 10 min, which was equivalent to the activity of 2 nM recombinant APE-1 protein in the molecular beacon assay. $EC_{2\,nM}$ of nuclear extracts was incubated with 2 to 500 nM hairpin DNA substrate and the $V_0$ measured for each value of [S]. Finally, the apparent $K_M^*$ was deduced using the software algorithm in Prism (as described previously), and the $K_M^*$ was used to determine the apparent $K_i^*$. Inhibition of $EC_{2\,nM}$ APE-1 activity by the inhibitors was assayed via the molecular beacon assay (described above).

Cytotoxic Effects of APE-1 Inhibitors on Cultured Human Glioblastoma (T98G) Cells. Human glioblastoma cells (T98G) were maintained in growth medium as described above. To assay short term cytotoxicity, T98G cells maintained in growth medium, were harvested by Trypsin-EDTA treatment, resuspended in fresh growth medium at a density of $10^4$ cells $mL^{-1}$, and 200 µL (2000 cells) of this suspension was seeded into the wells of a sterile 96-well tissue culture plate. The cells were allowed to attach and grow for 24 h, and then treated with serial dilutions of the drug for 72 h. After treatment, viable cells were measured by an MTS assay using the CellTiter 96 AQueous kit (Promega) as per manufacturer's instructions. To assay long term cytotoxicity, T98G cells maintained in growth medium were harvested by Trypsin-EDTA treatment, resuspended in fresh growth medium at a density of 500 cells $mL^-$, and 200 µL (100 cells) of this suspension seeded into the wells of a sterile 96-well tissue culture plate. The cells were allowed to attach and grow for 24 h and treated with serial dilutions of the drug for 240 h. After treatment, viable cells were measured using the CyQUANT cell proliferation assay kit (Invitrogen) as per manufacturer's instructions.

Cytotoxic Potentiation of Various DNA Damaging Agents. T98G cells maintained in growth medium were resuspended in fresh growth medium and seeded into 96-well plates at 2000 cells/well (short term cytotoxicity) or 100 cells/well (long term cytotoxicity) as described in the previous section. After 24 h, the cells were treated with serial dilutions of various DNA damaging drugs in absence or presence of APE-1 inhibitors. At the end of the treatment period, cell survival was assayed using CellTiter 96 AQueous or CyQUANT kits for the short- and long-term studies respectively.

Quantification of Abasic Sites. T98G cells maintained in growth medium, were harvested by Trypsin-EDTA treatment, resuspended in fresh growth medium at a density of $2.5 \times 10^5$ cells $mL^{-1}$, and 2 mL ($5 \times 10^5$ cells) of this suspension was seeded into the wells of a sterile 6-well tissue culture plate. Cells were allowed to grow for 24 h, treated with the various compounds for different time points and/or at different concentrations. At the end of each treatment, adherent cells were harvested by trypsin-EDTA treatment and pooled with live and dead cells in culture supernatant. Pooled cells in suspension were pelleted by centrifugation, washed with 1×PBS and genomic DNA was isolated using the DNAzol reagent (Invitrogen). DNA in solution was quantified by UV absorbance ($\lambda_{260\,nm}$) using a Synergy H1 multiwell plate reader (BioTek, Winooski, Vt.). Abasic sites in purified DNA were then reacted with the biotin-conjugated aldehyde reactive probe (ARP), immobilized onto 96-well ELISA plates, and detected using horseradish peroxidase (HRP)-conjugated streptavidin using a colorimetric substrate as per manufacturer's instructions (Dojindo Molecular Technologies, Rockville, Md.).

Results and Discussion

The development of small molecule inhibitors of APE-1 has been challenging because of the structure around the protein's active site that is rich in basic amino acid residues, which make salt bridge contacts with the DNA phosphate backbone. An Arg residue on a flexible loop region moves into the DNA stack and occupies the vacancy created when the abasic lesion is extruded into the protein's active site. The hydrophobic face of the synthetic THF abasic site analogue in the crystal structure of APE-1 interacts with amino acid residues that create a hydrophobic pocket; however, the physiologically relevant 2-hydroxy-THF abasic site could form an H-bond via the 1'-α-hydroxyl group that is missing in the THF lesion.

Virtual Screening for Small-Molecule Inhibitors of APE-1. In silico screening was performed using the Surflex-dock program and established docking protocols based on the X-ray crystallographic data of APE-1 (1DEW.PDB). The predicted binding pocket was validated through 3D database docking searches and confirmed through experiments using the in silico screened hits (discussed below). FIG. 1 shows a docking pose of inhibitor 4 (Table 1) in the predicted binding pocket with the methylenedioxy ring mimicking the furan ring of the abasic site substrate in the X-ray co-crystallographic structure of APE-1. Analysis of the docking results reveal H-bonding interactions of compound 4 with Asn174 (2.33 Å), Thr268 (2.67 Å) and hydrophobic interactions (2.66~3.0 Å) of the dioxoloquinoline moiety with Phe266 and Trp280 as well as the carbazole ring with a hydrophobic domain (Trp280, Met271 and Val278). In the X-ray structure, the hydrophobic face of the extra-helical abasic lesion packs within a complementary APE-1 pocket formed by the side chains of Phe266, Trp280, and Leu282. In addition, Asn174, Asn212 and His309 also interact through H-bonds with the phosphate that is 5' of the abasic site target. Our docking also predicted that the basic Arg177 side chain could interact with the aromatic quinoline ring of compound 4 via a Π-cation interaction (3.42 Å).

Figure 7:
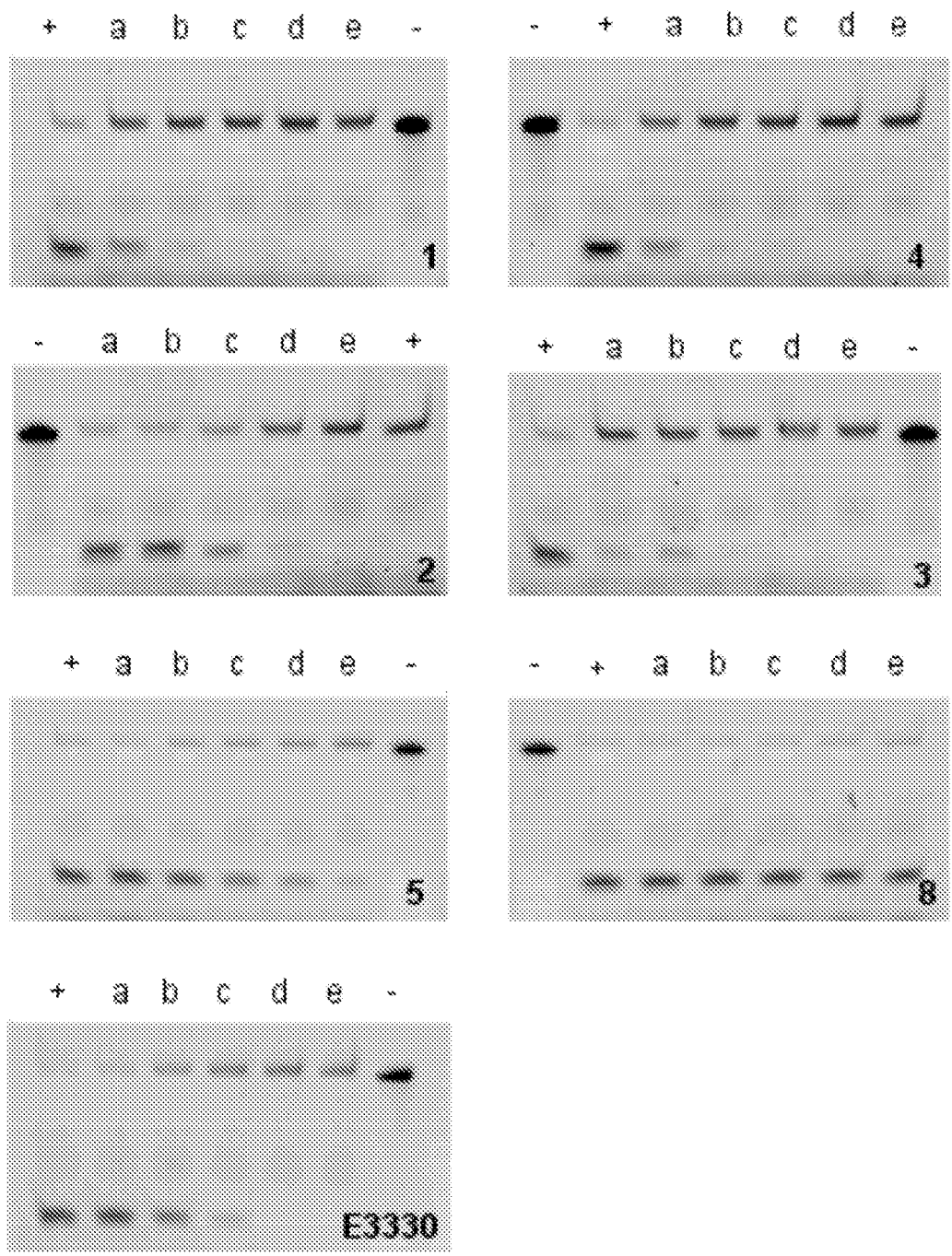
FIG. 7. Gel based assay measuring the inhibition of APE-1 endonuclease activity by compounds 1-5, 8 and E3330 (upper band, uncleaved 30 nucleotide THF-modified DNA; lower band, endonuclease cleaved 11 nucleotide fragment): +, control (no inhibitor); -, uncleaved target; a-e, 5, 10, 25, 50 and 100 µM compound, respectively.

Screening for APE-1 Inhibitors. The initial assessment of the molecules suggested by the computational study employed a molecular beacon approach similar to that previously described. In this assay, the DNA hairpin substrate has a 6-FAM fluorophore on the 5'-terminus, a DABA-CYL fluorescence quencher on the 3'-terminus and a THF abasic site located 6 base pairs from the 5'-terminus in the stem region (FIG. 6). APE-1 activity is monitored as an increase in fluorescence due to the release of the 5'-(6-FAM)-GCACT fragment as a function of time. Compounds that had good inhibitory activity ($K_i \leq 10$ μM) in the molecular beacon screen were then retested using a gel-based assay to directly measure DNA excision as a function of inhibitor concentration (FIG. 7). This second assay, which directly measures the amount and site of DNA nicking confirms that the endonuclease processing of the abasic lesion is inhibited and eliminates the possibility of artifacts that can arise in the fluorescence measurements or from random nuclease activity. In this assay, substrate turnover was calculated from relative intensities of cleaved vs. intact oligomers and correlated with inhibitor concentration. Using this approach, the $IC_{50}$ values (Table 2) were estimated for APE-1 inhibition by 1 (4.4 μM), 2 (10.1 μM), 3 (2.9 μM), 4 (4.1 μM), 5 (34.4 μM), 8 (>100 μM) and E3330 (14.7 μM). The inhibitory activity ($K_i$) observed in the molecular beacon assay (Table 1) correlated in all cases with the $IC_{50}$ activity in the gel assay (Table 2). Of the thirty compounds (Table 1) evaluated based on the modeling, six showed a $K_i$ of <1.0 μM in the molecular beacon assay (Table I). It was not possible to fully characterize some of the compounds because of their limited solubility. The relatively high hit rate in the molecular beacon assay is attributed to the success of the molecular modeling to predict structures in contrast to a random screen of a large chemical library. The importance of the benzo[d][1,3]dioxole structure and H-bond donor at position-$N^4$ on the quinoline ring, which were predicted from the modeling, was evident from the assays. For example, compounds I and 8 are identical except for the methylenedioxy substitution on the quinoline ring, yet their effect on APE-1 activity differs by more than 50-fold. The dramatic difference between 1 and 7 also illustrates the important role of the dioxole ring. The appendage on the hydrazone had less impact on the in vitro inhibition. Compounds 1-5 and 8 were selected for additional evaluation based on the range of their in vitro activity.

In addition to the compounds identified from the modeling studies, E3330, a previously reported inhibitor that has been shown to interact with the endonuclease active site of APE-1, (Manvilla et al. Biochemistry 50, 82-92 (2011)) was tested for comparative purposes. The $K_i$ for E3330 is our system was 2.2 μM in the molecular beacon assay (FIG. 6C) and the $IC_{50}$ in the gel assay was 14.7 μM (FIG. 7). In order to probe the potential role of DNA intercalation as a mechanism for APE-1 inhibition (see below), ethidium bromide (EtBr) was evaluated. It showed a $K_i$ of 1.8 μM in the molecular beacon assay (FIG. 6C) but its intercalating and fluorescence properties hindered analysis in the gel assay.

Figure 8:
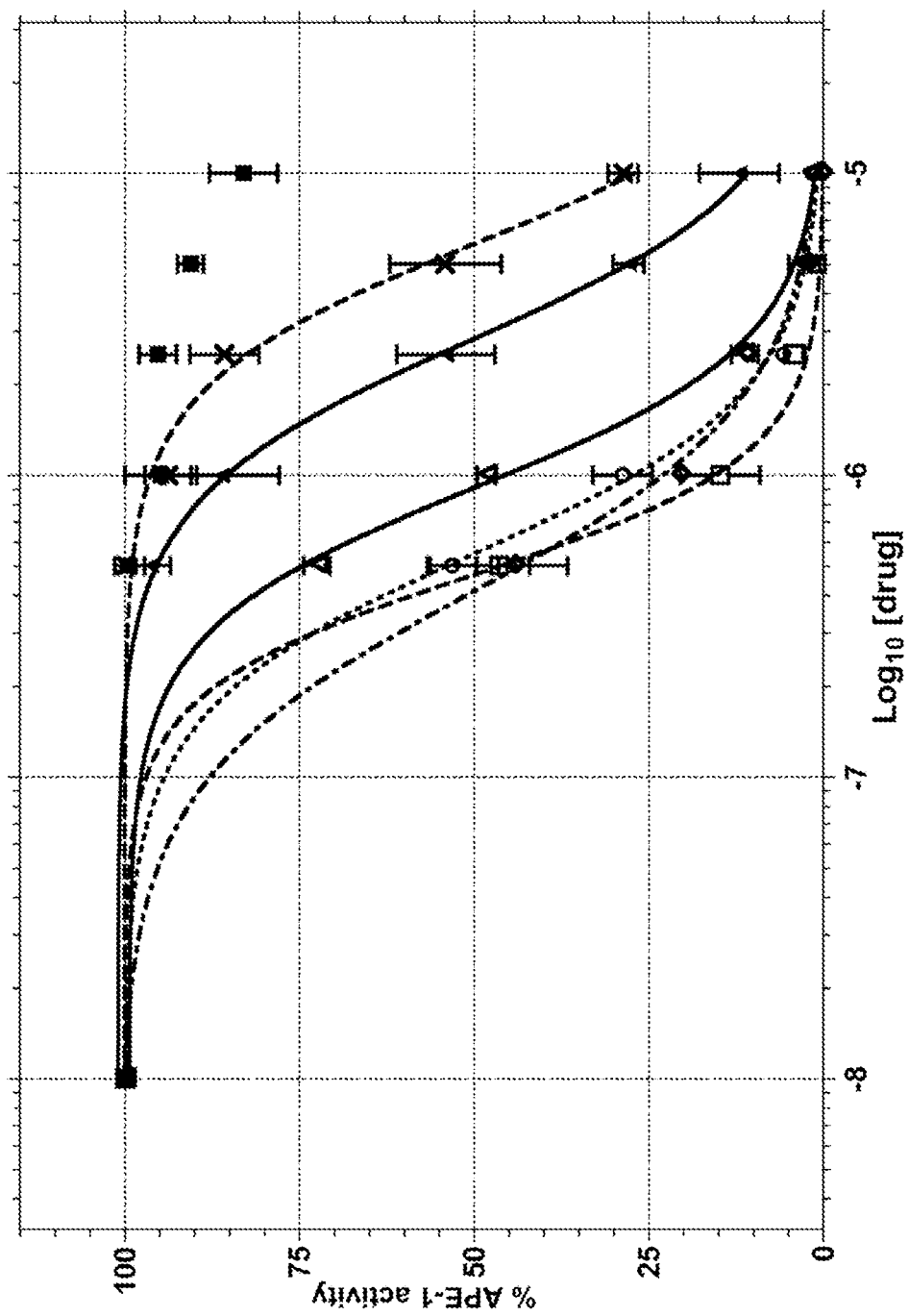
FIG. 8. Inhibition of APE-1 endonuclease activity by 1 (Δ), 2 (□), 3(○), 4 (◇), 5 (▲), 8 (■) and E3330 (X) in T98G cell nuclear extracts in molecular beacon assay (see FIG. 6 for details).

Inhibition of APE-1 Activity in Nuclear Lysates. The ability of 1-5 and 8 to block APE-1 endonuclease activity in a complex mixture of proteins from T98G cell nuclear lysates was tested using the molecular beacon assay. The APE-1 activity in the lysates was standardized to give ~90% turnover of 25 nM substrate in 10 min. This activity is similar to that of 2 nM recombinant APE-1 used in the molecular beacon assay. The $K_M$ and $V_{max}$ of $EC_{2\,nM}$ APE-1 activity in nuclear lysates were determined to be 24.4 nM and 8.5 fluorescence units (arbitrary) $min^{-1}$, respectively. Using these values, the $K_i$ for 1-5 was calculated to be 0.45, 0.24, 0.28, 0.21 and 1.41 μM, respectively. For comparison E3330 had a $K_i$ of 2.93 μM. Compounds 1-4 clearly blocked excision of the target DNA with the abasic site analogue in the presence of the nuclear lysate that contain APE-1 activity (FIG. 8). These results indicate that compounds 1-5 have reasonable selectivity even in the complex mixture of proteins in the nuclear lysates.

Figure 9A:
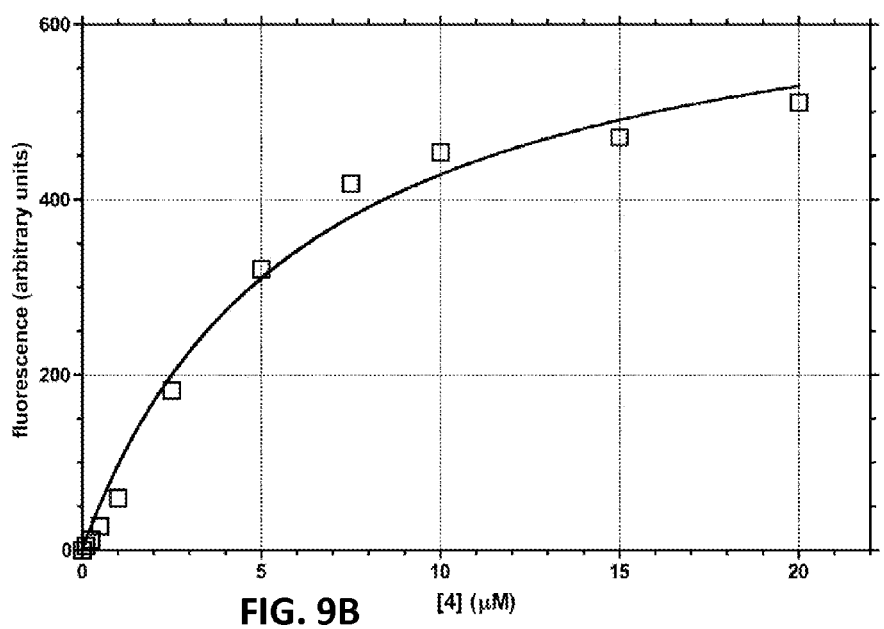
FIG. 9. Concentration dependent change in the fluorescence of 4 in the presence of 1 µM APE-1: (A) binding of 4 to APE-1 as measured by the increase in fluorescence (excitation at 395 nm, emission at 510 nm); $K_D$ of 6.15 µM; (B) displacement of 4 from APE-1 by E3330 measured by decrease in the fluorescence of 4.
Figure 9B:
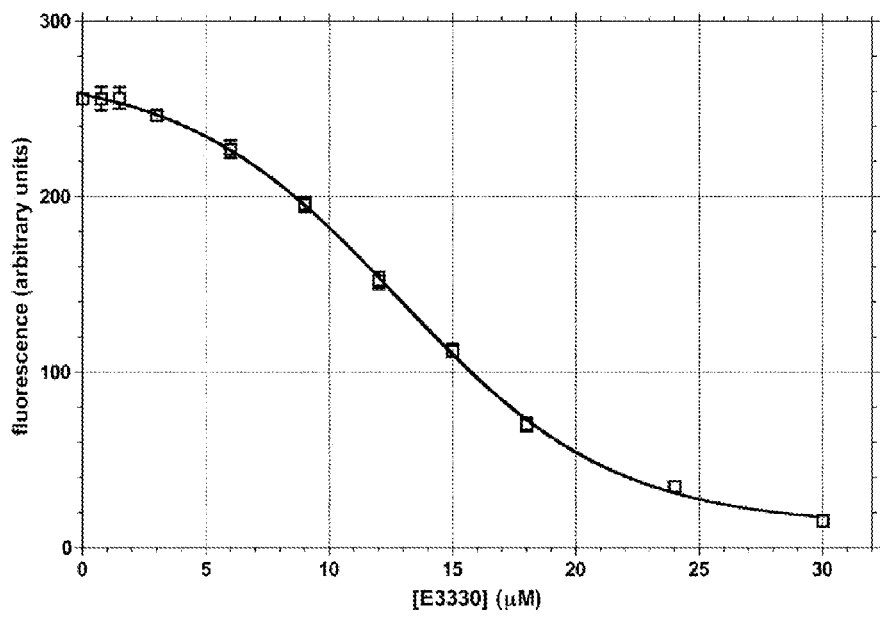

Interaction of Inhibitors with APE-1 Protein. To establish whether there is a direct interaction between an inhibitor and APE-1, the fluorescence spectra of 4 was determined in the absence and presence of increasing amounts of the protein. Compound 4 is the only potent inhibitor that is fluorescent in buffer (containing 0.5% DMSO) with an excitation at 395 nm and a broad emission maximum at 485-520 nm. In the presence of APE-1, there is a concentration-dependent enhanced fluorescence of 4 (FIG. 9), which suggests a physical interaction with the protein that reduces fluorescence quenching due to interaction with solvent. The emission maximum also shifts with the 485 nm band increasing to a smaller extent than the long wavelength band, which is displaced by 10 nm to 510 nm. These data suggest direct binding between the protein and the inhibitor. E3330 is an APE-1 inhibitor for which there are NMR data showing an interaction with the protein's active site. Therefore, compound 4 (6.0 μM) was incubated with APE-1 (1 μM) and measured the change in fluorescence upon the addition of 0.5 to 10.0 μM E3330 (FIG. 9). The results show that there is an E3330 concentration-dependent displacement of 4 from the protein as indicated by the decrease in 4's fluorescence intensity. To obtain approximately 50% decrease in the fluorescence of 6 μM 4, requires approximately 12 μM E3330. E3330 binds to APE-1 with a $K_D$ of 55 μM from the NMR study and causes a 3-fold inhibition of APE-1 endonuclease activity at 100 μM concentration in a gel based excision assay. The $IC_{50}$ for E3330 redox inhibition is 10 μM. The displacement of 4 from APE-1 by E3330 indicates that 4 binds to, or near, the endonuclease site of the protein.

Interaction of Inhibitors with DNA. A potential mechanism by which compounds can block APE-1 activity involves the interaction with the DNA substrate by intercalation. Such binding to DNA could sterically reduce the accessibility of the protein to the abasic site substrate. The intercalation of compounds that have planar aromatic systems is common and relevant because the abasic lesion potentially provides a high affinity site for the planar compounds to enter into the DNA base stack. The interaction of 1, which exhibits no fluorescence in solution, with an unmodified DNA oligomer and one with an abasic site causes a concentration dependent increase in fluorescence intensity (FIG. 10). Compound 4 shows a similar fluorescence response. To further probe the potential role of intercalation, the effect of EtBr on the fluorescence of 1 and 4 were determined. Ethidium is a well-characterized intercalator that has a $K_D$ near 1 µM with double-stranded DNA, although it binds almost 10-fold stronger to DNA with a bulge. However, similar $K_D$'s for EtBr with the unmodified and THF modified hairpin DNA of 1.6 and 1.8 µM were observed, respectively. The fluorescence enhancement of 1 and 4 in the presence of DNA was significantly muted by the presence of EtBr suggesting competitive binding to the DNA. Of note, is that 1 appears to exhibit a strong preference for DNA containing the THF abasic site based on the difference in the fluorescence intensities (FIG. 10). The small changes in the fluorescence of 4 with both DNAs indicate little discrimination for the THF lesion. A similar pattern was observed in the effect of 1 and 4 on the thermal stability of DNA as determined by UV melting experiments using several DNA substrates. With the self-complementary sequence 5'-GAGAGCGCTCTC, 1 increased the $T_M$ from 36.4 to 40.8° C. while the $T_M$ for this sequence with 4 was unchanged (37.3° C.). Using the unmodified hairpin DNA has shown in FIG. 10B, we observed a similar effect: $\Delta T_M$ was 4° C. with 1 and 0.5° C. with 4. The stability of the hairpin with the THF abasic site increased by >9° C. in the presence of 1, but not appreciably with 4. These data suggest weak binding between DNA and 4, while 1 clearly has a stronger interaction with both unmodified DNA and DNA with a THF abasic site.

In summary, both 1 and 4 can bind to DNA, presumably by intercalation, but the binding is relatively weak, as compared to EtBr, and non-specific and cannot explain their ability to inhibit APE-1 endonuclease activity at nM concentrations in the different assays. Consistent with this conclusion is the weaker inhibition of APE-1 endonuclease activity by EtBr, which has a higher affinity for DNA than 1 or 4. The overall evidence is consistent with inhibitor 4 acting by binding directly to the protein. The mechanism of action for some of the other inhibitors remains to be experimentally determined.

Figure 11A:
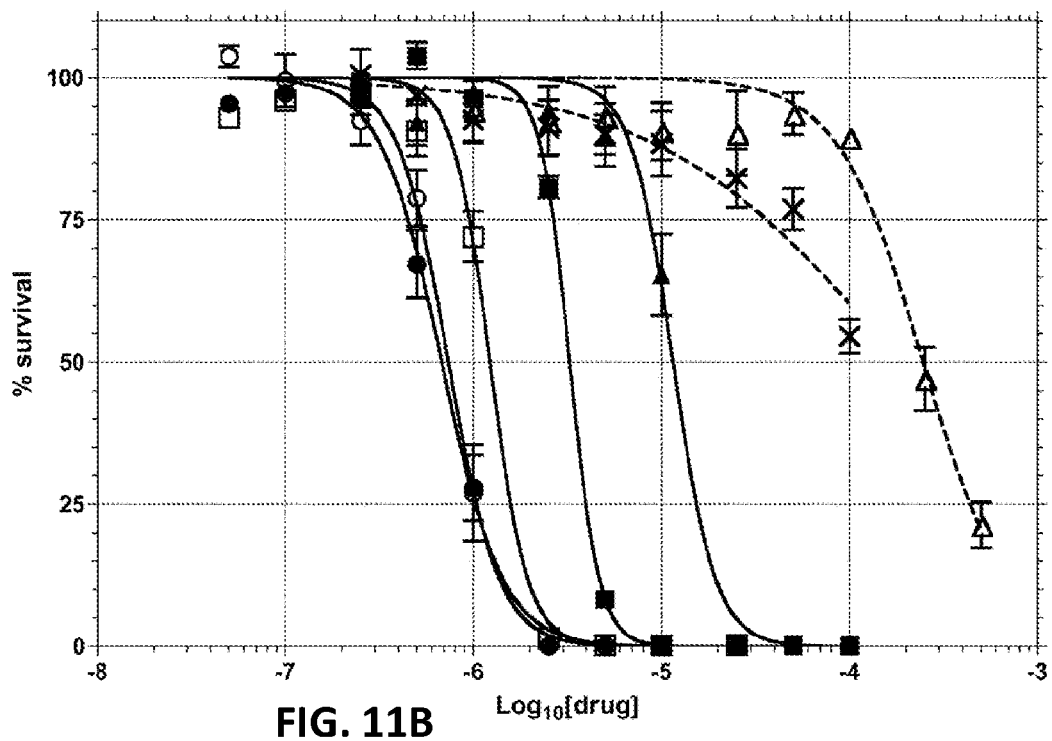
FIG. 11. The toxicity of compounds 1 (■), 2 (□), 3 (●), 4 (○), 5 (▲), MeLex (Δ) and E3330 (X) were determined in T98G cells: (A) short term (72 h) MTS assay; (B) 10-day Cyquant assay.
Figure 11B:
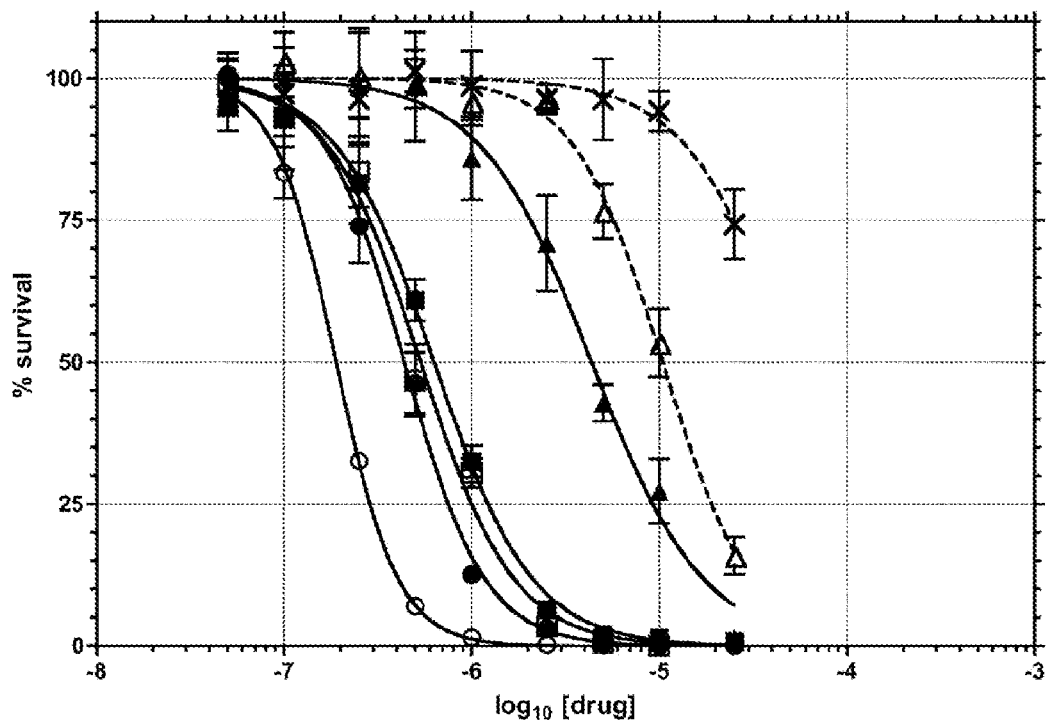
Figure 12A:
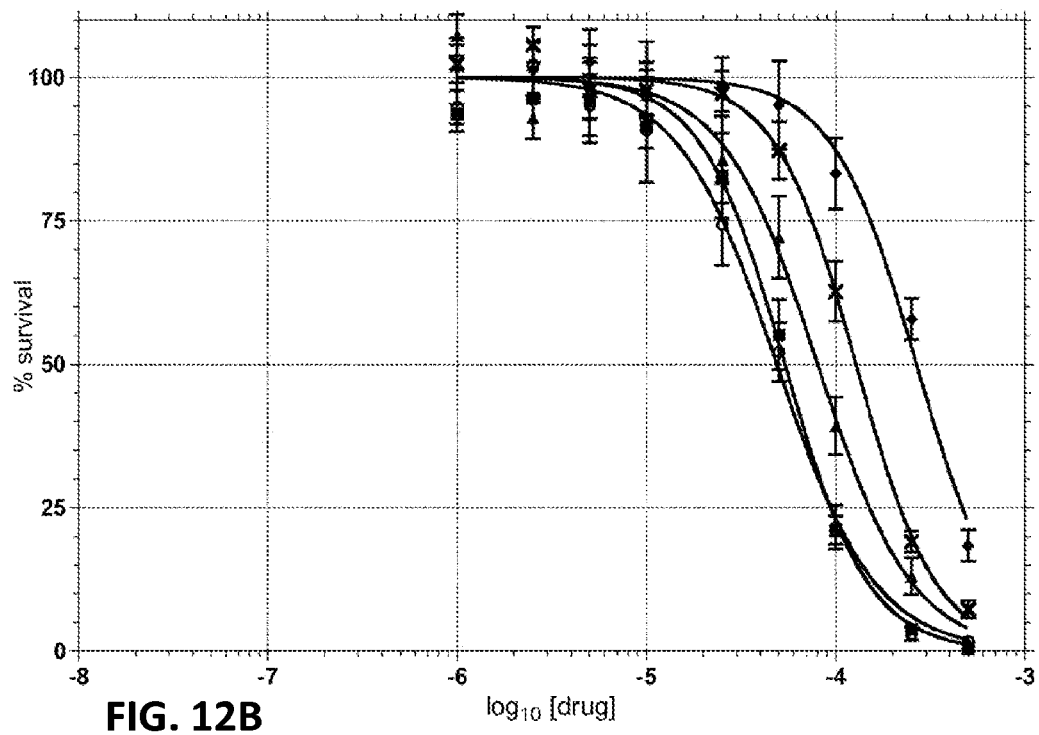
FIG. 12. The potentiation of MeLex cytotoxicity was determined in T98G cells treated with different concentrations of MeLex alone (◆) or in combination with $LD_{10}$ concentrations of 1 (■), 4 (○), 5 (▲), or E3330 (X). (A) short-term (72 h) MTS assay; (B) long term (10 d) CyQUANT assay.
Figure 12B:
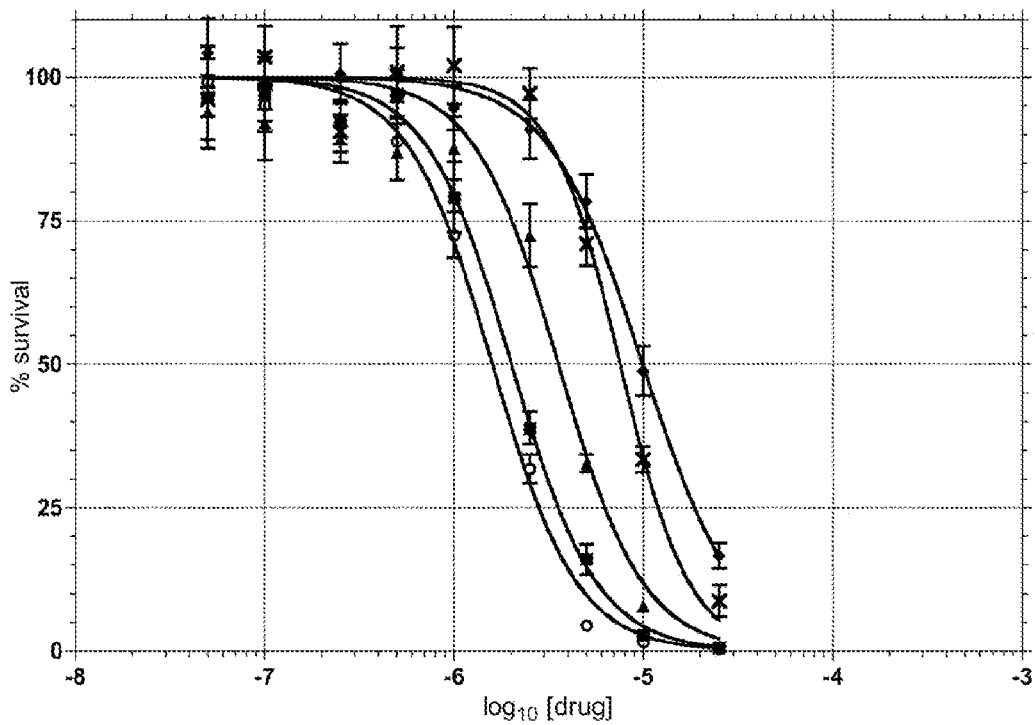

Toxicity. It was assumed that inhibition of APE-1 activity would be lead to toxicity since genetic deletion of the protein is lethal to cells. Therefore, the toxicities of compounds I-5 and E3330 were determined in human T98G glioma cells using both short-term (3-day) MTS (FIG. 11A) and long term (10-day) CyQUANT (FIG. 11B) assays. The toxicities were also determined in combination with the DNA minor groove methylating agent, MeLex. MeLex efficiently and selectively generates N3-methyladenine, which is converted into an abasic site by a BER glycosylase and/or hydrolytic depurination. The T98G cell line is relatively resistant to DNA damaging anticancer agents due to expression of multiple drug resistance proteins and $O^6$-alkylguanine-DNA alkyltransferase. Compound 4 was again the most active with an $LD_{50}$ of 960 nM in the MTS assay and 190 nM in the clonogenic assay. The toxicities of compounds 1-3 were all approximately 500 nM in the long term assay and <5 µM in the short term assay, while 5 was almost 20-fold less toxic than 4. Of note, E3330 was approximately 250- and 750-fold less toxic to the cells than 4 in the short- and long-term assays, respectively. The previously reported E3330 $IC_{50}$ for cell growth in HEYC-2 and SKOV-3× ovarian tumor cells is ~35 µM. As a reference, the methylating agent, MeLex showed an $LD_{50}$ of 250 and 12 µM in the short and long term cytotoxicity assays, respectively. The mechanism responsible for the toxicity of the inhibitor compounds remains to be determined, but their activities generally correlate with the $K_i$ for in vitro APE-1 inhibition (Table I) suggesting that the decrease in APE-1 activity is involved. A goal of the development of APE-1 inhibitors is to determine if they can be used to enhance the activity of DNA alkylating agents. Therefore, we tested how the $LD_{10}$ concentrations of compounds 1 (2.20 µM), 4 (0.25 µM) and 5 (6.50 µM) affected the toxicity of MeLex (FIG. 12) in the 72 h MTS assay. The $LD_{50}$ of MeLex dropped from 267 µM by itself to 54, 49 and 80 µM in the presence of 1, 4 and 5, respectively (FIG. 12A). When an $LD_{10}$ concentration of E3330 (6.9 µM) was combined with MeLex, the cells were only 2-fold more sensitive to MeLex (128 µM). In a long term assay the corresponding $LD_{10}$ concentrations of 1 (0.17 µM), 4 (0.08 µM), and 5 (0.90 µM) caused a decrease in the $LD_{50}$ of MeLex (9.9 µM) to 2.0, 1.6 and 3.6 µM respectively. E3330 (14.80 µM) had little or no contribution towards potentiating the toxicity of MeLex (FIG. 12B). Overall the maximum potentiation (i.e., with 4) of MeLex was approximately 5-fold for both the short and long term assays.

Some of the tested compounds are closely related to a series of molecules evaluated for antimalarial and antitubercular activity. The $IC_{50}$ for the toxicity of compound 3 in a VERA kidney cell line was determined to be 630 nM, which compares to the 540 nM that we observed in the glioma T98G line (Table 1). The origin of the toxicity in the VERA cells was not determined but the inhibition of APE-1 would be predicted to be toxic in all cells.

Figure 13A:
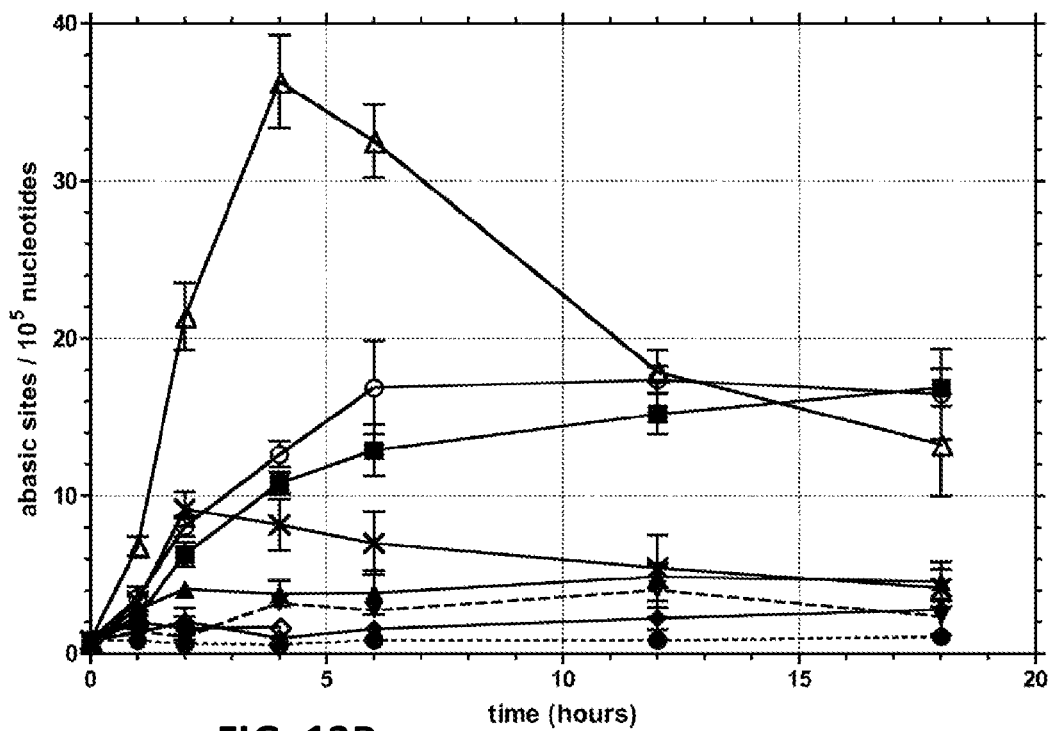
FIG. 13. Formation of aldehyde reactive sites (ARS, abasic sites) was quantified in: (A) cells treated with 0.25 µM 1 (■), 4 (○), 5 (▲), 8 (◇), E3330 (X), EtBr (▼) or 80 µM MeLex (Δ); (B) cells treated with combinations of 80 µM MeLex ($LD_{10}$) and 0.25 µM of 1 (■), 4 (○), 5 (▲), E3330 (X), EtBr (▼). Controls employed in both sets were untreated cells (●) or cells treated with 0.2% DMSO (◆).

Formation of Abasic Sites. To confirm that the inhibitors were actually affecting the cellular processing of abasic sites, a biotinylated aldehyde reactive probe (Biotin-ARP) was used to measure the level of aldehyde reactive sites (ARS) in genomic DNA isolated from T98G cells that were incubated with the different inhibitors. The biotin tagged ARS are quantified using an avidin-biotin assay, followed by colorimetric detection with horseradish peroxidase conjugated to avidin. While the method does not specifically measure abasic DNA sites, it is assumed that most of the increase in signal results from an increase in the ring-opened form of abasic sites. The background level of ARS in untreated or 0.25% DMSO treated T98G cells was $\frac{1}{10^5}$ nucleotides, which is similar to previous reports (FIG. 13a). In the presence of 0.25 µM 4 (FIG. 13), which corresponds to less than the $LD_{10}$ concentration due to the 25-fold increase in the number of cells used in the ARS vs. the toxicity assay (FIG. 11), there was a continuous increase over the initial 6 h. The level of approximately 17 ARS/$10^5$ nucleotides was maintained until the final 18 h time point. Because the concentration of the inhibitors is below the $LD_{10}$, it is unlikely that a significant percentage of the ARS measured are in dead cells. However, it cannot be ruled out that ARS levels may rise in cells entering or in apoptosis. Therefore, it is not possible to unequivocally say that the accumulation of ARS leads to cell death or vice versa. A more detailed time course for markers of cell death and the build-up of ARS may resolve this issue.

At 0.25 µM, 1 showed a similar effect, but 5, which is a weaker inhibitor of APE-1 endonuclease activity (Table I), had a less dramatic effect with an increase in ARS of approximately 4-fold above background. The number of ARS with 0.25 μM 8 was the same as background. For comparison, 0.25 μM E3330 caused an increase in ARS similar to 1 and 4 at 2 h but then the number of lesions began to drop and returned to control levels by 18 h. EtBr was also evaluated at similar concentrations to determine if a strong intercalator could affect ARS levels. It had no effect on the formation of ARS. As a positive control for the formation of ARS, the cells were treated with 80 μM of MeLex. This MeLex treatment afforded a rapid induction of ARS ($36/10^5$ nucleotides) through the first 4 h that then decreased through 18 h to a value similar to that observed with 1 and 4. The rapid increase in ARS from MeLex through the first 4 h is consistent with the DNA methylation time course, while the gradual decrease of ARS levels is attributed to their removal by functional BER.

Figure 13B:
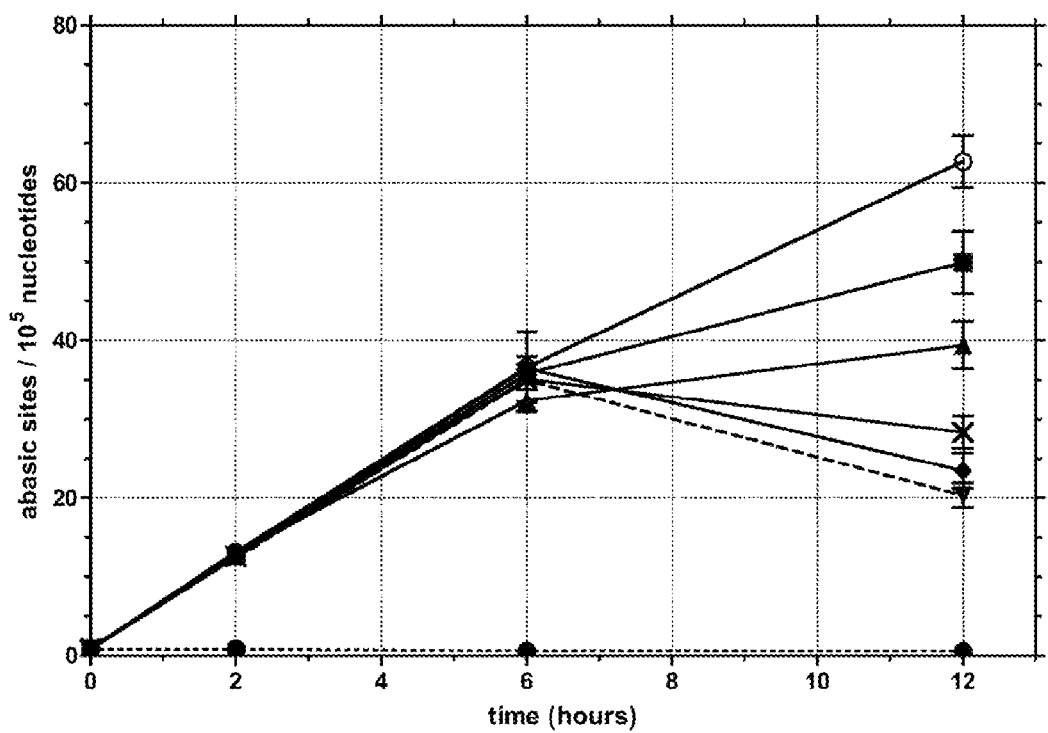

The effect of APE-1 inhibitors in combination with 80 μM MeLex was also determined (FIG. 13b). At the time points employed in the assays, the level of ARS reflects the kinetics of 3-mA lesion formation due to MeLex, and BER processing of the lesion by MPG excision, APE-1 cleavage at the abasic site and dRP lyase or flap endonuclease removal of the aldehyde functionality from the DNA. The level of ARS induced by MeLex by itself or with the different inhibitor compounds was not significantly different at the 2 or 6 h time points. However, the number of lesions dropped off with MeLex alone or with either 0.25 μM E3330 or EtBr. In contrast, the levels of ARS continued to increase through at least 12 h when MeLex was combined with 0.25 μM of the more potent inhibitors 1 (50 sites/$10^5$ nucleotides) or 4 (63 sites/$10^5$ nucleotides). Therefore, the combination of DNA methylation and APE-1 inhibition has the effect of sustaining an elevated level of ARS, which correlates with the enhancement of MeLex toxicity.

APE-1 Redox Activity. APE-1 has a redox activity that is associated with the regulation of specific transcriptional factors. To probe whether any of the molecules identified as APE-1 endonuclease inhibitors affected the redox activity, the ability of APE-1 to affect Jun/Fos binding to an SP-1 cognate DNA sequence was determined using a gel shift assay as described previously. E3330 was used as a positive control. No effect was observed with 100 μM concentration of 1-5 and 8 (data not shown), which is far above the concentration required to inhibit endonuclease activity. In summary, the compounds that are potent inhibitors of APE-1 endonuclease activity increase the persistence of ARS and synergistically affect the toxicity of a DNA methylating agent that generates lesions that are repaired by BER.

TABLE 1

Structures of compounds identified from in silico screen and APE-1 endonuclease inhibition ($K_i$).

| Name | NCI# | Structure | $K_i$ (μM)$^a$ |
|---|---|---|---|
| 1 | NSC332398 | 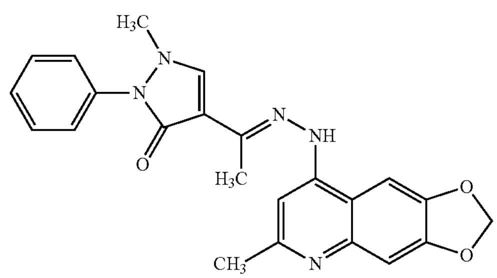 [SMILES: C/C(=N\Nc1cc(C)nc2cc3c(cc12)OCO3)c1cn(C)n(-c2ccccc2)c1=O] | 0.18 |
| 2 | NSC332384 | 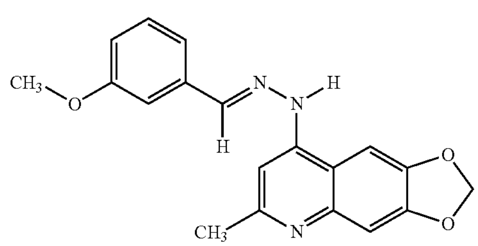 [SMILES: COc1cccc(/C=N/Nc2cc(C)nc3cc4c(cc23)OCO4)c1] | 0.22 |
| 3 | NSC332389 | 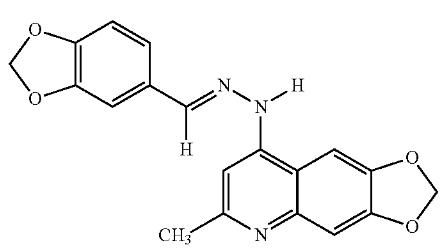 [SMILES: Cc1cc(N/N=C/c2ccc3c(c2)OCO3)c2cc3c(cc2n1)OCO3] | 0.19 |

TABLE 1-continued

Structures of compounds identified from in silico screen and APE-1 endonuclease inhibition ($K_i$).

| # | NSC ID | $K_i$ |
|---|--------|-------|
| 4 | NSC332395 | 0.12 |
| 5 | NSC332396 | 0.68 |
| 6 | NSC332397 | 0.64 |
| 7 | NSC300598 | 10.89 |
| 8 | NSC332410 | ND[b] |
| 9 | NSC89640 | 13.00 |

TABLE 1-continued
Structures of compounds identified from in silico screen and APE-1 endonuclease inhibition ($K_i$).
| 10 | NSC107215 | 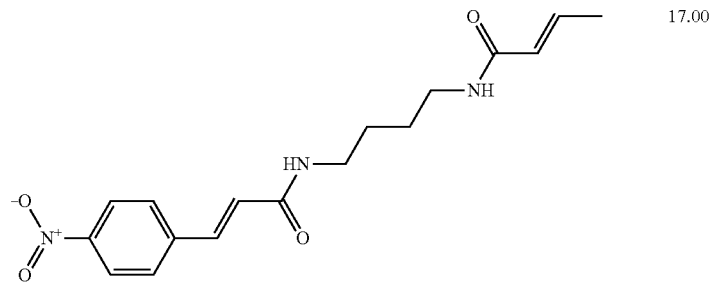 | 17.00 |
| 11 | NSC131534 | 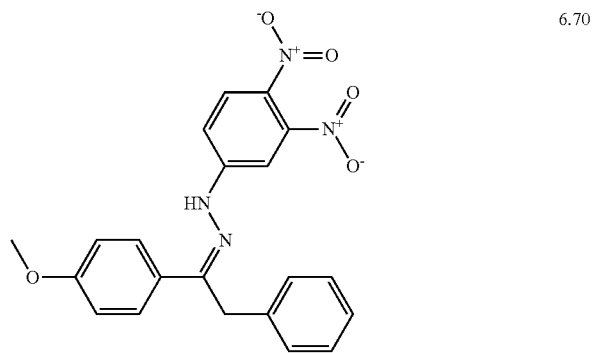 | 6.70 |
| 12 | NSC375491 | 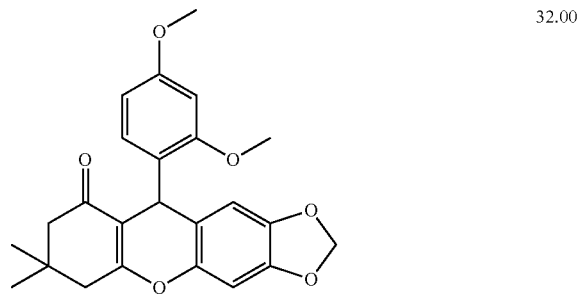 | 32.00 |
| 13 | NSC614430 | 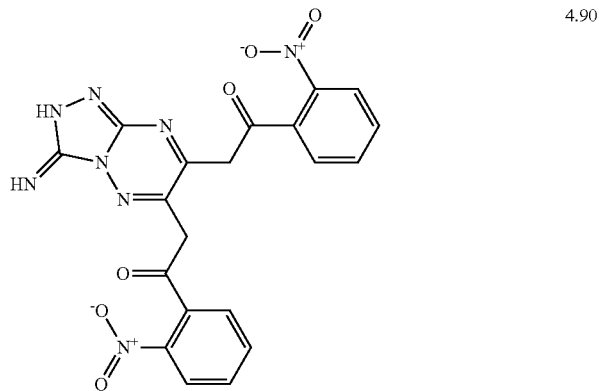 | 4.90 |

TABLE 1-continued
Structures of compounds identified from in silico screen and APE-1 endonuclease inhibition ($K_i$).
| | | | |
|---|---|---|---|
| 14 | NSC402686 | 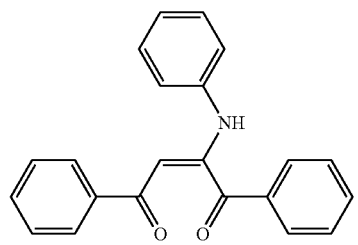 [SMILES: O=C(/C=C(/Nc1ccccc1)C(=O)c1ccccc1)c1ccccc1] | 37.00 |
| 15 | NSC658900 | 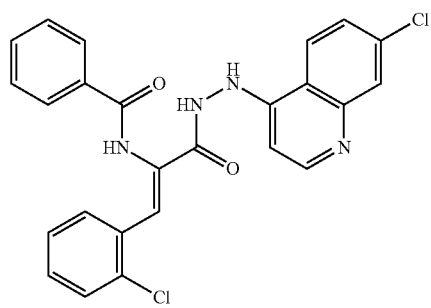 [SMILES: O=C(NNc1ccnc2cc(Cl)ccc12)/C(=C/c1ccccc1Cl)NC(=O)c1ccccc1] | ND |
| Name NCI# | Structure | $K_i$ ($\mu$M) |
|---|---|---|
| 16 NSC163444 | 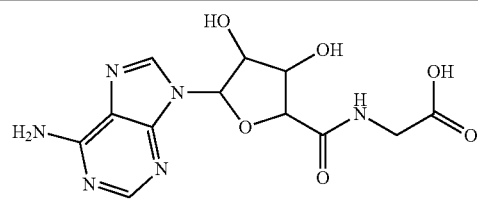 [SMILES: Nc1ncnc2c1ncn2C1OC(C(=O)NCC(=O)O)C(O)C1O] | ND |
| 17 NSC115605 | 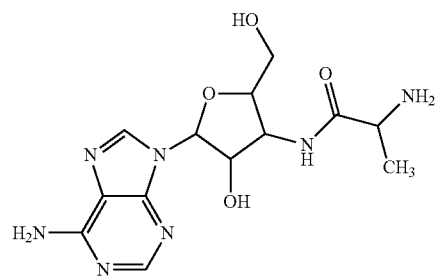 [SMILES: CC(N)C(=O)NC1C(CO)OC(n2cnc3c(N)ncnc32)C1O] | ND |
| 18 NSC128335 | 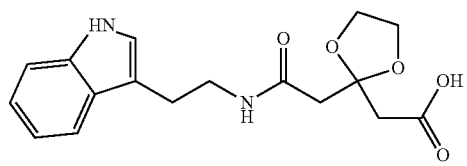 [SMILES: O=C(O)CC1(CC(=O)NCCc2c[nH]c3ccccc23)OCCO1] | ND |
| 19 NSC372329 | 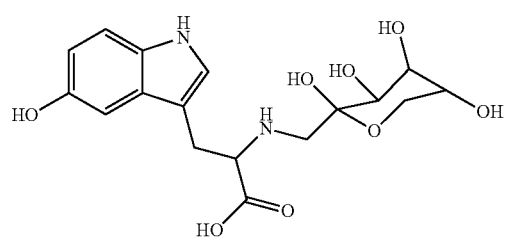 [SMILES: O=C(O)C(Cc1c[nH]c2ccc(O)cc12)NCC1(O)OCC(O)C(O)C1O] | ND |

TABLE 1-continued
Structures of compounds identified from in silico screen and APE-1 endonuclease inhibition ($K_i$).
| 20 | NSC283787 | 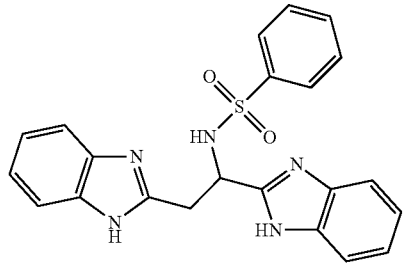 | ND[d] |
| 21 | NSC11847 | 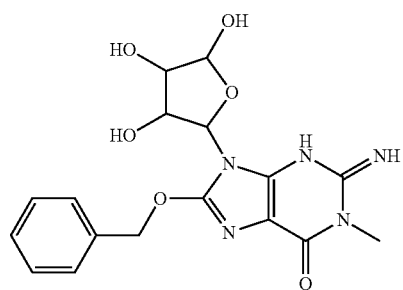 | ND |
| 22 | NSC117589 | 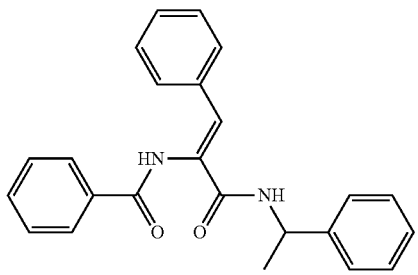 | ND |
| 23 | NSC126939 | 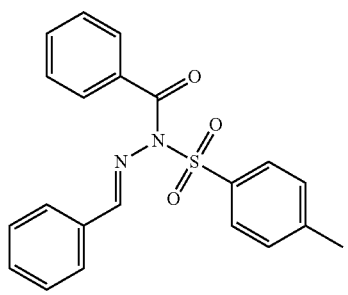 | ND[d] |
| 24 | NSC296950 | 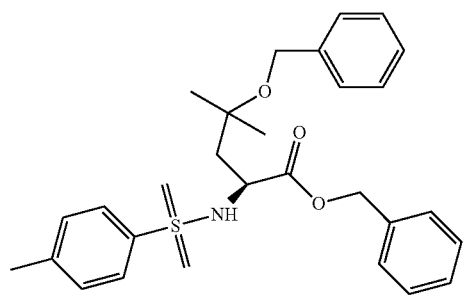 | ND[d] |

TABLE 1-continued

Structures of compounds identified from in silico screen and APE-1 endonuclease inhibition ($K_i$).

| | | | |
|---|---|---|---|
| 25 | NSC343032 | | ND |
| 26 | NSC374123 | | ND |
| 27 | NSC63636 | | ND[d] |
| 28 | CS-965570[c] | | ND |
| 29 | CS-565759[c] | | ND |

TABLE 1-continued

Structures of compounds identified from in silico screen and APE-1 endonuclease inhibition ($K_i$).

| | | | |
|---|---|---|---|
| 30 | CS-2504743[c] | 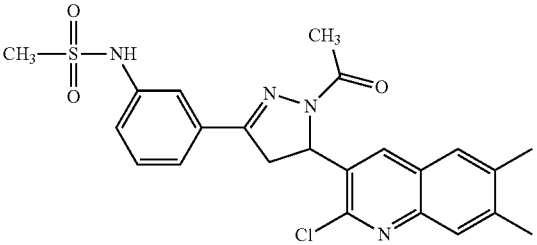 | ND |

[a] endonuclease activity.
[b] no detectable activity ($K_i$ > 100 μM).
[c] Chemspider accession number
[d] insufficient solubility in buffer containing 0.25% DMSO to determine if $K_i$ is >100 μM.

TABLE 2

IC$_{50}$ values for compounds 1, 2, 3, 4, 5, 8 and E3330 were calculated from the in gel excision assay by quantifying the relative intensities of the APE-1 cleaved fragment vs. full length DNA substrate in the absence or presence of potential APE-1 inhibitors.

| Compound | IC$_{50}$ (μM) |
|---|---|
| 1 | 4.4 |
| 2 | 10.1 |
| 3 | 2.9 |
| 4 | 4.1 |
| 5 | 34.4 |
| 8 | >100 |
| E3330 | 14.7 |

In view of the many possible embodiments to which the principles of the disclosed compounds, compositions, and methods may be applied, it should be recognized that the illustrated embodiments are only preferred examples of the invention and should not be taken as limiting the scope of the invention.

What is claimed is:

1. A method of inhibiting AP endonuclease-1/redox factor-1 (hAPE1) activity in a tumor cell resistant to DNA damaging agents comprising application to the tumor cell of a compound having the structure:

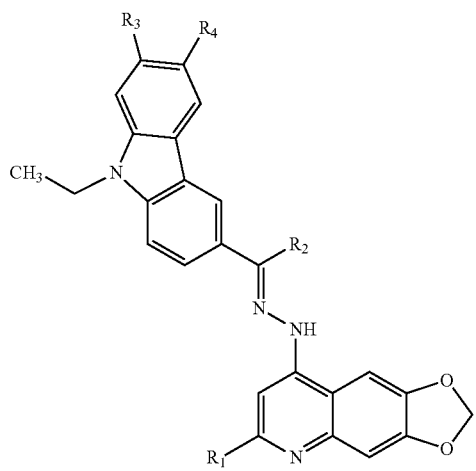

wherein $R_1$ is H, a C1-C5 alkyl group, which can be branched, unbranched, cyclic or acyclic, or a 3-5 member ring, which can be homocyclic or heterocyclic; $R_2$ is H, or a C1-C5 branched, unbranched, cyclic or acyclic alkyl group, and $R_3$ and $R_4$ are independently and separately H, a C1-C5 alkyl group, which can be branched, unbranched, cyclic or acyclic, or a 3-5 member ring, which can be homocyclic or heterocyclic.

2. A method of inhibiting AP endonuclease-1/redox factor-1 (hAPE1) activity in a tumor cell resistant to DNA damaging agents comprising application to the tumor cell of a compound having the structure

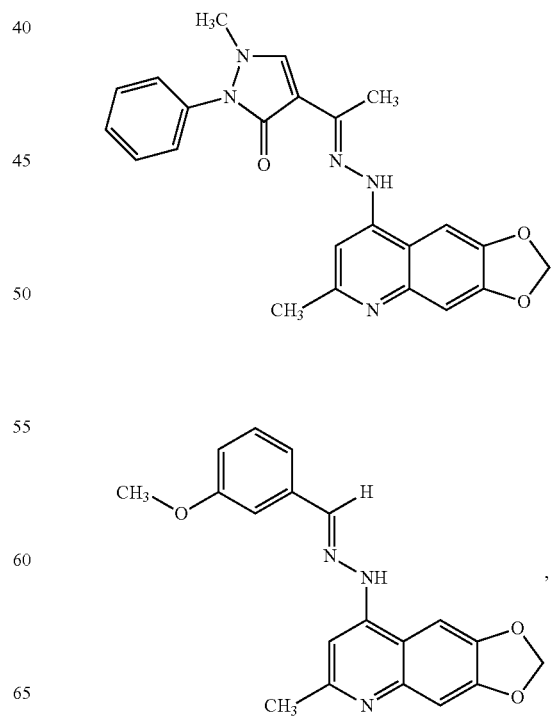

-continued

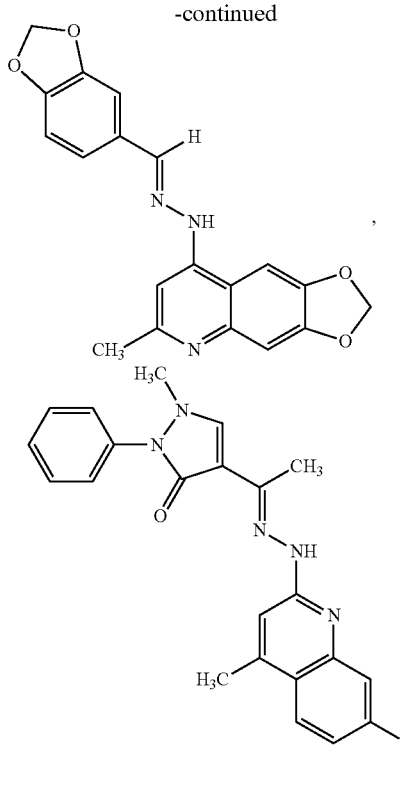

3. A method of inhibiting AP endonuclease-1/redox factor-1 (hAPE1) activity in a tumor cell resistant to DNA damaging agents comprising application to the tumor cell of a compound having the structure:

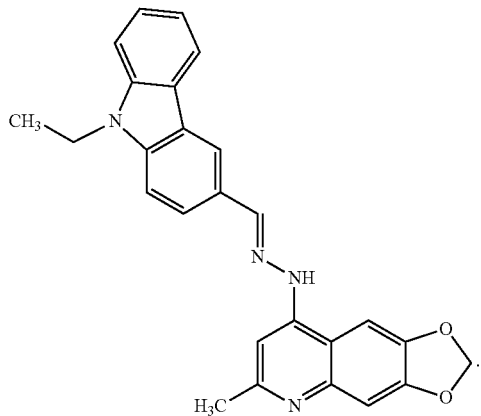 [SMILES: CCn1c2ccccc2c2cc(/C=N/Nc3cc(C)nc4cc5c(cc34)OCO5)ccc21]

4. A method for treating cancer in a subject, comprising administering to the subject a therapeutically effective amount of

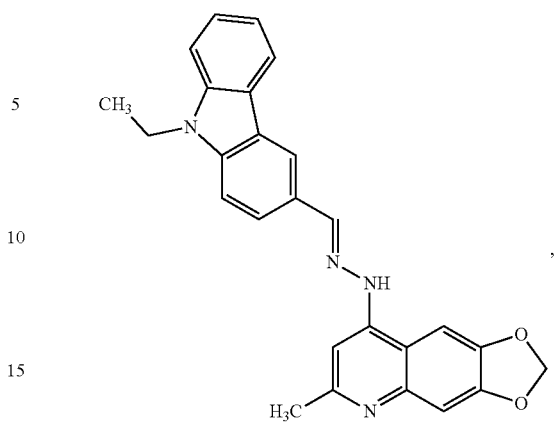

or a pharmaceutically acceptable salt thereof,
wherein the cancer is selected from human acute lymphoblastic leukemia, human chronic myelogenous leukemia, human myeloma, human large cell immunoblastic lymphoma, or human melanoma.

5. A method for treating glioma, wherein the glioma is resistant to a DNA damaging agent, in a subject, comprising co-administering to the subject a DNA damaging anticancer agent and a compound having a structure of:

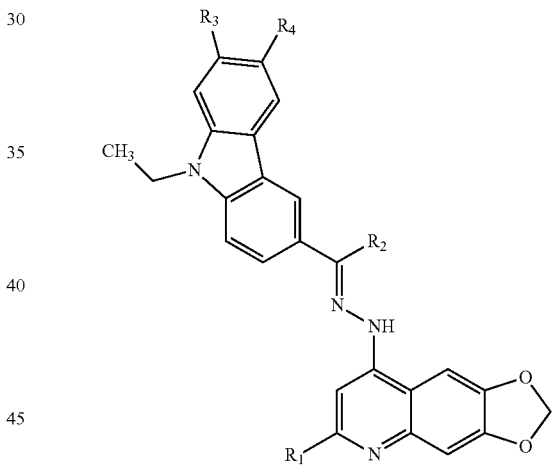

wherein $R_1$ is H, a C1-C5 alkyl group, which can be branched, unbranched, cyclic or acyclic, or a 3-5 member ring, which can be homocyclic or heterocyclic; $R_2$ is H, or a C1-C5 branched, unbranched, cyclic or acyclic alkyl group, and $R_3$ and $R_4$ are independently and separately H, a C1-C5 alkyl group, which can be branched, unbranched, cyclic or acyclic, or a 3-5 member ring, which can be homocyclic or heterocyclic.

* * * * *

```
SEQUENCE LISTING

<160> NUMBER OF SEQ ID NOS: 1

<210> SEQ ID NO 1
<211> LENGTH: 318
<212> TYPE: PRT
<213> ORGANISM: Homo sapiens

<400> SEQUENCE: 1

Met Pro Lys Arg Gly Lys Lys Gly Ala Val Ala Glu Asp Gly Asp Glu
1               5                   10                  15

Leu Arg Thr Glu Pro Glu Ala Lys Lys Ser Lys Thr Ala Ala Lys Lys
            20                  25                  30

Asn Asp Lys Glu Ala Ala Gly Glu Gly Pro Ala Leu Tyr Glu Asp Pro
        35                  40                  45

Pro Asp Gln Lys Thr Ser Pro Ser Gly Lys Pro Ala Thr Leu Lys Ile
    50                  55                  60

Cys Ser Trp Asn Val Asp Gly Leu Arg Ala Trp Ile Lys Lys Lys Gly
65                  70                  75                  80

Leu Asp Trp Val Lys Glu Glu Ala Pro Asp Ile Leu Cys Leu Gln Glu
                85                  90                  95

Thr Lys Cys Ser Glu Asn Lys Leu Pro Ala Glu Leu Gln Glu Leu Pro
            100                 105                 110

Gly Leu Ser His Gln Tyr Trp Ser Ala Pro Ser Asp Lys Glu Gly Tyr
        115                 120                 125
```

```
Ser Gly Val Gly Leu Leu Ser Arg Gln Cys Pro Leu Lys Val Ser Tyr
    130                 135                 140
Gly Ile Gly Asp Glu Glu His Asp Gln Glu Gly Arg Val Ile Val Ala
145                 150                 155                 160
Glu Phe Asp Ser Phe Val Leu Val Thr Ala Tyr Val Pro Asn Ala Gly
                165                 170                 175
Arg Gly Leu Val Arg Leu Glu Tyr Arg Gln Arg Trp Asp Glu Ala Phe
                180                 185                 190
Arg Lys Phe Leu Lys Gly Leu Ala Ser Arg Lys Pro Leu Val Leu Cys
            195                 200                 205
Gly Asp Leu Asn Val Ala His Glu Glu Ile Asp Leu Arg Asn Pro Lys
210                 215                 220
Gly Asn Lys Lys Asn Ala Gly Phe Thr Pro Gln Glu Arg Gln Gly Phe
225                 230                 235                 240
Gly Glu Leu Leu Gln Ala Val Pro Leu Ala Asp Ser Phe Arg His Leu
                245                 250                 255
Tyr Pro Asn Thr Pro Tyr Ala Tyr Thr Phe Trp Thr Tyr Met Met Asn
            260                 265                 270
Ala Arg Ser Lys Asn Val Gly Trp Arg Leu Asp Tyr Phe Leu Leu Ser
            275                 280                 285
His Ser Leu Leu Pro Ala Leu Cys Asp Ser Lys Ile Arg Ser Lys Ala
    290                 295                 300
Leu Gly Ser Asp His Cys Pro Ile Thr Leu Tyr Leu Ala Leu
305                 310                 315
```